(12) United States Patent
Frame et al.

(10) Patent No.: US 11,642,478 B2
(45) Date of Patent: May 9, 2023

(54) BREATHING ASSISTANCE APPARATUS WITH SERVICEABILITY FEATURES

(71) Applicant: Fisher & Paykel Healthcare Limited, Auckland (NZ)

(72) Inventors: Samuel Robertson Frame, New Plymouth (NZ); Christopher Malcolm Crone, Auckland (NZ); Christopher Simon James Quill, Auckland (NZ); Kevin Peter O'Donnell, Auckland (NZ); Jack Che-Wei Hsu, Manukau (NZ); Jae Chul Han, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 348 days.

(21) Appl. No.: 16/938,549

(22) Filed: Jul. 24, 2020

(65) Prior Publication Data

US 2021/0077758 A1    Mar. 18, 2021

Related U.S. Application Data

(63) Continuation of application No. 15/668,603, filed on Aug. 3, 2017, now Pat. No. 10,758,692, which is a
(Continued)

(51) Int. Cl.
*A61M 16/00* (2006.01)
*G16H 40/63* (2018.01)
(Continued)

(52) U.S. Cl.
CPC .... *A61M 16/0051* (2013.01); *A61M 16/0003* (2014.02); *A61M 16/0057* (2013.01);
(Continued)

(58) Field of Classification Search
CPC .......... A61M 16/0051; A61M 16/0003; A61M 16/0672; A61M 16/1005; A61M 16/109;
(Continued)

(56) References Cited

U.S. PATENT DOCUMENTS 3,893,458 A    7/1975  Fletcher et al.
4,110,419 A    8/1978  Miller
(Continued)

FOREIGN PATENT DOCUMENTS

AU    2013244091    4/2013
AU    2018203137    5/2018
(Continued)

OTHER PUBLICATIONS

PCT International Search Report for PCT/NZ2013/000060 dated Jul. 22, 2013, 10 pages.
(Continued)

*Primary Examiner* — Steven O Douglas
(74) *Attorney, Agent, or Firm* — Knobbe, Martens, Olson & Bear LLP

(57) ABSTRACT

A breathing assistance apparatus is configured with features that improve serviceability of the apparatus. The apparatus can include animations to provide instruction regarding correcting easily-identified fault conditions and to provide instruction regarding routine maintenance routines. The apparatus also can be configured with top level control menus that are obscured in a manner to limit manipulation of the top level control elements by unauthorized users.

23 Claims, 21 Drawing Sheets

Related U.S. Application Data continuation of application No. 14/505,298, filed on Oct. 2, 2014, now Pat. No. 9,737,675, which is a continuation of application No. PCT/NZ2013/000060, filed on Apr. 5, 2013.

(60) Provisional application No. 61/620,676, filed on Apr. 5, 2012.

(51) Int. Cl.
| | |
|---|---|
| *G16H 40/40* | (2018.01) |
| *A61M 16/06* | (2006.01) |
| *A61M 16/10* | (2006.01) |
| *A61M 16/16* | (2006.01) |
| *G16H 20/40* | (2018.01) |
| *A61M 16/08* | (2006.01) |

(52) U.S. Cl.
CPC ...... *A61M 16/024* (2017.08); *A61M 16/0672* (2014.02); *A61M 16/0875* (2013.01); *A61M 16/105* (2013.01); *A61M 16/1005* (2014.02); *A61M 16/109* (2014.02); *A61M 16/1075* (2013.01); *A61M 16/1095* (2014.02); *A61M 16/16* (2013.01); *A61M 16/161* (2014.02); *G16H 20/40* (2018.01); *G16H 40/40* (2018.01); *G16H 40/63* (2018.01); *A61M 16/0816* (2013.01); *A61M 16/107* (2014.02); *A61M 2016/003* (2013.01); *A61M 2016/0039* (2013.01); *A61M 2016/1025* (2013.01); *A61M 2202/0208* (2013.01); *A61M 2205/12* (2013.01); *A61M 2205/14* (2013.01); *A61M 2205/18* (2013.01); *A61M 2205/27* (2013.01); *A61M 2205/3334* (2013.01); *A61M 2205/3368* (2013.01); *A61M 2205/3375* (2013.01); *A61M 2205/3386* (2013.01); *A61M 2205/36* (2013.01); *A61M 2205/502* (2013.01); *A61M 2205/581* (2013.01); *A61M 2205/75* (2013.01); *A61M 2230/42* (2013.01); *A61M 2230/435* (2013.01)

(58) Field of Classification Search
CPC ............ A61M 16/1095; A61M 16/161; A61M 16/024; A61M 16/0057; A61M 16/0875; A61M 16/105; A61M 16/1075; A61M 16/16; A61M 16/107; A61M 16/0816; A61M 2016/003; G16H 20/40; G16H 40/40; G16H 40/63
See application file for complete search history.

(56) References Cited

U.S. PATENT DOCUMENTS

| | | | |
|---|---|---|---|
| 5,602,625 A | 2/1997 | Okamoto et al. | |
| 5,696,686 A | 12/1997 | Sanka et al. | |
| 5,931,160 A | 8/1999 | Gilmore et al. | |
| 6,283,132 B1 | 9/2001 | Stephens et al. | |
| 6,361,518 B1 | 3/2002 | Brierton et al. | |
| 6,523,538 B1 | 2/2003 | Wikefeldt | |
| 6,750,878 B1 | 6/2004 | Tatsuo et al. | |
| 8,511,651 B2 | 8/2013 | Fridberg et al. | |
| 8,555,881 B2 | 10/2013 | Wallace et al. | |
| 8,733,349 B2 | 5/2014 | Bath et al. | |
| 8,741,220 B2 | 6/2014 | O'Donnell et al. | |
| 8,739,780 B2 | 7/2014 | Tang et al. | |
| 8,944,057 B2 | 2/2015 | Hill et al. | |
| 9,526,807 B2 | 12/2016 | O'Donnell et al. | |
| 9,693,848 B2 | 7/2017 | Dunlop | |
| 9,737,675 B2 | 8/2017 | Frame et al. | |
| 9,844,636 B2 | 12/2017 | McGroary et al. | |
| 10,493,225 B2 | 12/2019 | Thiessen | |
| 10,512,702 B2 | 12/2019 | O'Donnell et al. | |
| 10,758,692 B2 | 9/2020 | Frame et al. | |
| 11,033,699 B2 | 6/2021 | Oates et al. | |
| 2002/0124847 A1 | 9/2002 | Smith et al. | |
| 2002/0151804 A1 | 10/2002 | O'Mahoney et al. | |
| 2003/0062045 A1 | 4/2003 | Woodring et al. | |
| 2003/0209246 A1 | 11/2003 | Schroeder et al. | |
| 2004/0031756 A1 | 2/2004 | Suzuki et al. | |
| 2004/0079370 A1 | 4/2004 | Gradon et al. | |
| 2004/0261797 A1 | 12/2004 | White et al. | |
| 2006/0169281 A1 | 8/2006 | Aylsworth et al. | |
| 2007/0069922 A1 | 7/2007 | Adams et al. | |
| 2008/0048390 A1 | 2/2008 | Gutierrez-Vazquez et al. | |
| 2008/0053441 A1 | 3/2008 | Gottlib et al. | |
| 2008/0072900 A1 | 3/2008 | Kenyon et al. | |
| 2008/0310994 A1 | 12/2008 | O'Donnell et al. | |
| 2009/0275805 A1 | 11/2009 | Lane et al. | |
| 2010/0183320 A1 | 7/2010 | Yamada | |
| 2011/0132362 A1 | 6/2011 | Sanchez | |
| 2011/0138323 A1 | 6/2011 | Skidmore et al. | |
| 2011/0261411 A1 | 10/2011 | Mochizuki et al. | |
| 2011/0265024 A1 | 10/2011 | Leone et al. | |
| 2012/0055483 A1 | 3/2012 | Wilkinson et al. | |
| 2020/0171189 A1 | 6/2020 | O'Donnell et al. | |

FOREIGN PATENT DOCUMENTS

| | | |
|---|---|---|
| AU | 2020233691 | 9/2020 |
| CA | 2869140 | 4/2012 |
| EP | 2833954 | 2/2015 |
| EP | 3701991 | 9/2020 |
| JP | 4352965 | 12/1992 |
| JP | H08-252314 | 10/1996 |
| JP | H08-299307 | 11/1996 |
| JP | 2001-321443 | 11/2001 |
| JP | 2002-345965 | 12/2002 |
| JP | 2005-40589 | 2/2005 |
| TW | 2010/41615 | 12/2010 |
| WO | WO 2004/024429 | 3/2004 |
| WO | WO 2004/026382 | 4/2004 |
| WO | WO 2005/011785 | 2/2005 |
| WO | WO 2005/021076 | 3/2005 |
| WO | WO 2006/126900 A1 | 11/2006 |
| WO | WO 2007/069922 | 6/2007 |
| WO | WO 2009/058081 A1 | 5/2009 |
| WO | WO 2010/003064 | 1/2010 |
| WO | WO 2010/028427 | 3/2010 |
| WO | WO 2010/031125 A1 | 3/2010 |
| WO | WO 2011/050059 | 4/2011 |
| WO | WO 2011/056080 | 5/2011 |
| WO | WO 2013/151448 | 10/2013 |

OTHER PUBLICATIONS

PCT Written Opinion of the International Searching Authority for PCT/NZ2013/000060 completed Jul. 22, 2013, 7 pages.
PCT International Preliminary Report on Patentability with PCT Written Opinion for PCT/NZ2013/000060 dated Dec. 9, 2014, 8 pages.

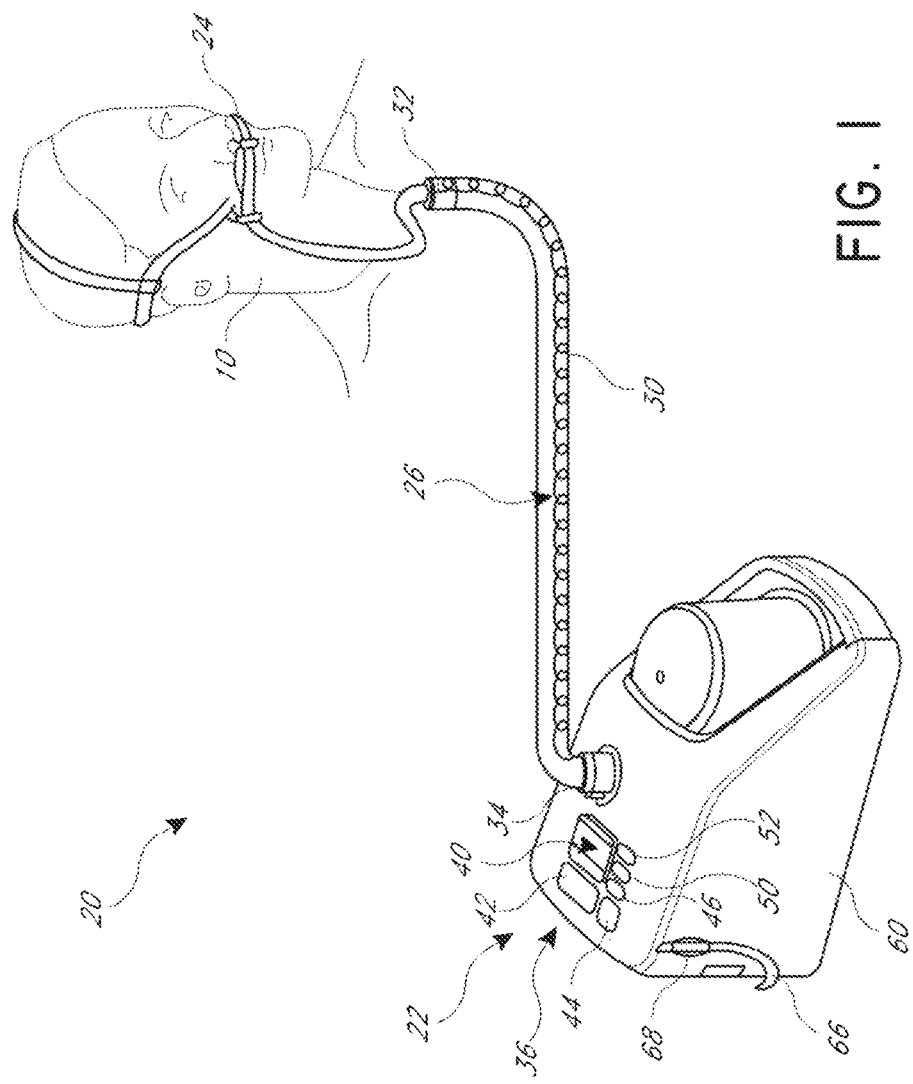

BREATHING ASSISTANCE APPARATUS WITH SERVICEABILITY FEATURES

CROSS-REFERENCE TO RELATED APPLICATIONS

This application is a continuation of U.S. patent application Ser. No. 15/668,603, entitled "Breathing Assistance Apparatus with Serviceability Features," filed Aug. 3, 2017, now U.S. Pat. No. 10,758,692, which is a continuation of U.S. patent application Ser. No. 14/505,298, entitled "Breathing Assistance Apparatus with Serviceability Features," filed Oct. 2, 2014, now U.S. Pat. No. 9,737,675, which is a continuation of International Application No. PCT/NZ2013/000060, entitled "Breathing Assistance Apparatus with Serviceability Features," filed Apr. 5, 2013, which claims the benefit of priority to U.S. Provisional Application No. 61/620,676, filed on Apr. 5, 2012. Each of the above-referenced applications is incorporated by reference herein in its entirety.

BACKGROUND

Field

The present disclosure generally relates to a gases supply and gases humidification apparatus. More particularly, features, aspects and advantages of the present disclosure relate to such apparatuses that can coach a user regarding the correction of a fault condition.

Description of the Related Art

A variety of machines can be used to assist with the breathing of a patient. Some of these machines are used among a plurality of users and are used almost continuously. Some of the machines are used by very few users and are used intermittently. These machines can deliver a heated and/or humidified flow of breathing gases to the user.

The machines may be operated by individuals and trained health professionals. From time to time, the machine may experience a condition that requires correction. For example, a breathing conduit could become detached or a breathing conduit could become at least partially blocked. In most instances, such conditions would be indicated by a numerical fault code. Such numerical fault codes would require the user or operator to consult a look-up table or call a technician. Often, this technique of correcting an easily corrected problem can be more time consuming than desired.

SUMMARY

Accordingly, a breathing apparatus comprises a flow generator, a humidifier chamber connected to the flow generator, a conduit connected to the humidifier generator, and a user breathing interface connected to the conduit. The apparatus also comprises a display screen adapted to provide visual information to a user. The apparatus monitors one or more characteristic of use and, upon a triggering event occurring, the apparatus provides a series of image frames such as, for example, graphics, recorded images, visual descriptions, visual directions, still images, and/or videos to the display. The series of image frames depict one or more still graphics and/or animated actions such that the user can make an adjustment to the apparatus based upon the image frames to address the occurrence of the triggering event.

In a first aspect, a breathing assistance apparatus is provided that includes a flow generator, a humidifier chamber connected to the flow generator, a conduit connected to the flow generator, a user breathing interface connected to the conduit, and a display screen adapted to provide visual information to a user. The apparatus can advantageously be configured to monitor one or more characteristics of use; and, upon an occurrence of a triggering event, to provide a series of image frames to the display. The series of image frames can depict an animated action that is configured to instruct a user to make an adjustment to the apparatus based upon the animated action to address the occurrence of the triggering event.

In some embodiments, the apparatus includes a button and depression of the button stops the display of the series of image frames. In some embodiments, the animated action includes a sequence that repeats until the triggering event is corrected.

In some embodiments, the triggering event comprises usage exceeding an upper limit of time. In a further embodiment, the animated action includes steps for replacing a filter.

In some embodiments, the triggering event comprises detection of at least one of a faulty heater wire, a faulty conduit temperature sensor, or a disconnected conduit. The animated action includes steps for replacing a breathing conduit.

In some embodiments, the triggering event comprises a reduction in resistance to flow. The animated action includes steps for reseating a chamber, reconnecting a conduit, or reconnecting an interface to the conduit.

In some embodiments, the triggering event comprises an increase in resistance to flow. The animated action includes steps for unbending a conduit, unclogging an interface, or checking that the correct interface is connected to the conduit.

In some embodiments, triggering event comprises detecting an oxygen level outside of a desired oxygen level. The animated action includes steps for adjusting the oxygen supply.

In some embodiments, the triggering event comprises detecting a low water supply level. The animated action includes steps for replenishing the water supply.

In some embodiments, the triggering event comprises detecting a presence of an oxygen supply during disinfection mode. The animated action includes steps for removing the oxygen supply. In a further embodiment, the apparatus is adapted to shut off power to a disinfection conduit heater until the triggering event is corrected.

In some embodiments, the triggering event comprises detecting disconnection, depletion, or prolonged interruption of an oxygen supply. The animated action includes steps for reconnecting the oxygen supply.

In some embodiments, the triggering event comprises failing to detect a breathing pattern. The animated action includes steps for reattaching a user interface.

In some embodiments, the triggering event comprises a breathing rate exceeding a predetermined breathing rate. The animated action includes illustrating the breathing rate.

In some embodiments, the triggering event comprises one of usage exceeding an upper limit of time, detecting a faulty heater wire, detecting a faulty conduit temperature sensor, detecting a disconnected conduit, a reduction in resistance to flow, an increase in resistance to flow, detecting an oxygen level outside of a desired oxygen level, detecting a low water supply level, detecting a presence of an oxygen supply during disinfection mode, detecting disconnection of an oxygen supply, detecting depletion or prolonged interruption of an oxygen supply, failing to detect a breathing pattern, or a breathing rate exceeding a predetermined breathing rate; and the animated action comprises a sequence that repeats until the triggering event is corrected.

In a second aspect, some embodiments provide for a breathing assistance apparatus that includes a flow generator, a humidifier chamber coupled to the flow generator, a conduit coupled to the flow generator, a user breathing interface connected to the conduit, a controller electrically coupled to the apparatus, a display screen electrically coupled to the controller and adapted to provide visual information to a user. The apparatus is configured to monitor one or more characteristics of use and to detect an occurrence of a triggering event using the controller, the detection of the triggering event being at least partly based on the monitored characteristics of use. The apparatus is also configured to select a series of image frames depicting an animated action and to provide the series of image frames to the display. The animated action can advantageously be configured to instruct a user to make an adjustment to the apparatus based upon the animated action to address the occurrence of the triggering event by providing visual cues in the series of image frames indicating a region of interest and at least one audible cue corresponding to an occurrence of an action in the series of image frames wherein the audible cue and the occurrence of the action are configured to be presented substantially simultaneously.

In some embodiments of the second aspect, the audible cue is configured to approximate a sound produced when the action occurs. In some embodiments of the second aspect, the visual cues comprise flashing lights surrounding the region of interest.

In some embodiments of the second aspect, the series of image frames comprises a first subset of image frames depicting the apparatus with a first level of detail and a second subset of image frames depicting a second level of detail, the second level of detail being greater than the first level of detail. In a further embodiment, the second subset of image frames presents a zoomed-in depiction of a portion of the apparatus that includes the region of interest.

In some embodiments, the one or more characteristics of use includes at least one of usage time, heater wire status, oxygen supply status, temperature sensor status, conduit status, water level, flow rate, resistance to flow, oxygen level, breathing rate, gas temperature, or heater plate power.

In some embodiments, the apparatus includes a button and depression of the button stops the display of the series of image frames. In some embodiments, the animated action includes a sequence that repeats until the triggering event is corrected.

In a third aspect, a method of indicating an alarm on a breathing assistance apparatus is provided. The method can include detecting an occurrence of a triggering event using a controller of the apparatus. The method can include selecting an animated action corresponding to the detected occurrence of the triggering event. The method can include displaying on a display of the apparatus a series of image frames depicting the animated action. The method can include detecting a correction of the triggering event using a controller of the apparatus. The method can include ending the display of the series of image frames upon detection of the correction of the triggering event. The series of image frames can advantageously be configured to instruct a user to make an adjustment to the apparatus based upon the animated action to address the occurrence of the triggering event.

In a fourth aspect, a method of indicating an alarm on a breathing assistance apparatus is provided. The method can include detecting a triggering event using a controller of the apparatus. The method can include selecting an animated action corresponding to the detected triggering event. The method can include displaying on a display of the apparatus a series of image frames depicting the animated action. The method can include emitting an audible noise with a speaker of the apparatus. The method can include detecting a correction of the triggering event using a controller of the apparatus. The method can include ending the display of the series of image frames and the emission of the audible noise upon detection of the correction of the triggering event. The series of image frames can advantageously be configured to instruct a user to make an adjustment to the apparatus based upon the animated action to address the triggering event by providing visual cues in the series of image frames indicating a region of interest and at least one audible cue corresponding to an occurrence of an action in the series of image frames. The audible cue and the occurrence of the action can advantageously be configured to be presented substantially simultaneously.

In some embodiments of the fourth aspect, the audible cue is configured to approximate a sound produced when the action occurs. In some embodiments of the fourth aspect, the visual cues comprise flashing lights surrounding the region of interest.

In some embodiments of the fourth aspect, the series of image frames comprises a first subset of image frames depicting the apparatus with a first level of detail and a second subset of image frames depicting a second level of detail, the second level of detail being greater than the first level of detail. In a further embodiment, the second subset of image frames presents a zoomed-in depiction of a portion of the apparatus that includes the region of interest.

In some embodiments of the fourth aspect, the method can include monitoring one or more characteristics of use. In a further embodiment, the one or more characteristics of use includes at least one of usage time, heater wire status, oxygen supply status, temperature sensor status, conduit status, water level, flow rate, resistance to flow, oxygen level, breathing rate, gas temperature, or heater plate power.

In summary, the disclosure may be described according to the following numbered clauses:

Clause 1. A breathing assistance apparatus comprising: a flow generator; a humidifier chamber connected to the flow generator; a conduit connected to the flow generator; a user breathing interface connected to the conduit; and a display screen adapted to provide visual information to a user, wherein the apparatus is configured to monitor one or more characteristics of use, and upon an occurrence of a triggering event to provide a series of image frames to the display, the series of image frames depicting an animated action configured to instruct a user to make an adjustment to the apparatus based upon the animated action to address the occurrence of the triggering event.

Clause 2. The apparatus of Clause 1, further comprising a button and depression of the button stops the display of the series of image frames.

Clause 3. The apparatus of Clause 1, wherein the triggering event comprises usage exceeding an upper limit of time.

Clause 4. The apparatus of Clause 3, wherein the animated action comprises steps for replacing a filter.

Clause 5. The apparatus of Clause 1, wherein the triggering event comprises detection of at least one of a faulty heater wire, a faulty conduit temperature sensor, or a disconnected conduit.

Clause 6. The apparatus of Clause 5, wherein the animated action comprises steps for replacing a breathing conduit.

Clause 7. The apparatus of Clause 1, wherein the triggering event comprises a reduction in resistance to flow.

Clause 8. The apparatus of Clause 7, wherein the animated action comprises steps for reseating a chamber, reconnecting a conduit or reconnecting an interface to the conduit.

Clause 9. The apparatus of Clause 1, wherein the triggering event comprises an increase in resistance to flow.

Clause 10. The apparatus of Clause 9, wherein the animated action comprises steps for unbending a conduit, unclogging an interface or checking that the correct interface is connected to the conduit.

Clause 11. The apparatus of Clause 1, wherein the triggering event comprises detecting an oxygen level outside of a desired oxygen level.

Clause 12. The apparatus of Clause 11, wherein the animated action comprises steps for adjusting the oxygen supply.

Clause 13. The apparatus of Clause 1, wherein the triggering event comprises detecting a low water supply level.

Clause 14. The apparatus of Clause 13, wherein the animated action comprises steps for replenishing the water supply.

Clause 15. The apparatus of Clause 1, wherein the triggering event comprises detecting a presence of an oxygen supply during disinfection mode.

Clause 16. The apparatus of Clause 15, wherein the animated action comprises steps for removing the oxygen supply.

Clause 17. The apparatus of Clause 16, wherein the apparatus also shuts off power to a disinfection conduit heater until the triggering event is corrected.

Clause 18. The apparatus of Clause 1, wherein the triggering event comprises detecting disconnection, depletion or prolonged interruption of an oxygen supply.

Clause 19. The apparatus of Clause 18, wherein the animated action comprises steps for reconnecting the oxygen supply.

Clause 20. The apparatus of Clause 1, wherein the triggering event comprises failing to detect a breathing pattern.

Clause 21. The apparatus of Clause 20, wherein the animated action comprises steps for reattaching a user interface.

Clause 22. The apparatus of Clause 1, wherein the triggering event comprises a breathing rate exceeding a predetermined breathing rate.

Clause 23. The apparatus of Clause 22, wherein the animated action comprises illustrating the breathing rate.

Clause 24. The apparatus of any of Clauses 3-23, wherein the animated action comprises a sequence that repeats until the triggering event is corrected.

Clause 24. The apparatus of Clause 1, wherein the triggering event comprises one of usage exceeding an upper limit of time, detecting a faulty heater wire, detecting a faulty conduit temperature sensor, detecting a disconnected conduit, a reduction in resistance to flow, an increase in resistance to flow, detecting an oxygen level outside of a desired oxygen level, detecting a low water supply level, detecting a presence of an oxygen supply during disinfection mode, detecting disconnection of an oxygen supply, detecting depletion or prolonged interruption of an oxygen supply, failing to detect a breathing pattern, or a breathing rate exceeding a predetermined breathing rate; and the animated action comprises a sequence that repeats until the triggering event is corrected.

Clause 25. A breathing assistance apparatus comprising: a flow generator; a humidifier chamber coupled to the flow generator; a conduit coupled to the flow generator; a user breathing interface connected to the conduit; a controller electrically coupled to the apparatus; and a display screen electrically coupled to the controller and adapted to provide visual information to a user, wherein the apparatus is configured to: monitor one or more characteristics of use; detect an occurrence of a triggering event using the controller, the detection of the triggering event being at least partly based on the monitored characteristics of use; select a series of image frames depicting an animated action; and provide the series of image frames to the display, wherein the animated action is configured to instruct a user to make an adjustment to the apparatus based upon the animated action to address the occurrence of the triggering event by providing visual cues in the series of image frames indicating a region of interest and at least one audible cue corresponding to an occurrence of an action in the series of image frames wherein the audible cue and the occurrence of the action are configured to be presented substantially simultaneously.

Clause 26. The apparatus of Clause 25, wherein the audible cue is configured to approximate a sound produced when the action occurs.

Clause 27. The apparatus of Clause 25, wherein the visual cues comprise flashing lights surrounding the region of interest.

Clause 28. The apparatus of Clause 25, wherein the series of image frames comprises a first subset of image frames depicting the apparatus with a first level of detail and a second subset of image frames depicting a second level of detail, the second level of detail being greater than the first level of detail.

Clause 29. The apparatus of Clause 28, wherein the second subset of image frames presents a zoomed-in depiction of a portion of the apparatus that includes the region of interest.

Clause 30. The apparatus of Clause 25, wherein the one or more characteristics of use includes at least one of usage time, heater wire status, oxygen supply status, temperature sensor status, conduit status, water level, flow rate, resistance to flow, oxygen level, breathing rate, gas temperature, or heater plate power.

Clause 31. The apparatus of Clause 25, wherein the triggering event comprises one of usage exceeding an upper limit of time, detecting a faulty heater wire, detecting a faulty conduit temperature sensor, detecting a disconnected conduit, a reduction in resistance to flow, an increase in resistance to flow, detecting an oxygen level outside of a desired oxygen level, detecting a low water supply level, detecting a presence of an oxygen supply during disinfection mode, detecting disconnection of an oxygen supply, detecting depletion or prolonged interruption of an oxygen supply, failing to detect a breathing pattern, or a breathing rate exceeding a predetermined breathing rate; and the animated action comprises a sequence that repeats until the triggering event is corrected.

Clause 32. The apparatus of Clause 31, wherein the animated action comprises steps for replacing a filter.

Clause 33. The apparatus of Clause 31, wherein the animated action comprises steps for replacing a breathing conduit.

Clause 34. The apparatus of Clause 31, wherein the animated action comprises steps for reseating a chamber, reconnecting a conduit or reconnecting an interface to the conduit.

Clause 35. The apparatus of Clause 31, wherein the animated action comprises steps for unbending a conduit, unclogging an interface or checking that the correct interface is connected to the conduit.

Clause 36. The apparatus of Clause 31, wherein the animated action comprises steps for adjusting the oxygen supply.

Clause 37. The apparatus of Clause 31, wherein the animated action comprises steps for replenishing the water supply.

Clause 38. The apparatus of Clause 31, wherein the animated action comprises steps for removing the oxygen supply.

Clause 39. The apparatus of Clause 38, wherein the apparatus also shuts off power to a disinfection conduit heater until the triggering event is corrected.

Clause 40. The apparatus of Clause 31, wherein the animated action comprises steps for reconnecting the oxygen supply.

Clause 41. The apparatus of Clause 31, wherein the animated action comprises steps for reattaching a user interface.

Clause 42. The apparatus of Clause 31, wherein the animated action comprises illustrating the breathing rate.

Clause 43. A method of indicating an alarm on a breathing assistance apparatus, the method comprising: detecting an occurrence of a triggering event using a controller of the apparatus; selecting an animated action corresponding to the detected occurrence of the triggering event; displaying on a display of the apparatus a series of image frames depicting the animated action; detecting a correction of the triggering event using a controller of the apparatus; and ending the display of the animated action upon detection of the correction of the triggering event, wherein the series of image frames are configured to instruct a user to make an adjustment to the apparatus based upon the animated action to address the occurrence of the triggering event.

Clause 44. A method of indicating an alarm on a breathing assistance apparatus, the method comprising: detecting a triggering event using a controller of the apparatus; selecting an animated action corresponding to the detected triggering event; displaying on a display of the apparatus a series of image frames depicting the animated action; emitting an audible noise with a speaker of the apparatus; detecting a correction of the triggering event using a controller of the apparatus; and ending the display of the animated action and the emission of the audible noise upon detection of the correction of the triggering event, wherein the animated action is configured to instruct a user to make an adjustment to the apparatus based upon the animated action to address the triggering event by providing visual cues in the series of image frames indicating a region of interest and at least one audible cue corresponding to an occurrence of an action in the series of image frames wherein the audible cue and the occurrence of the action are configured to be presented substantially simultaneously.

BRIEF DESCRIPTION OF THE DRAWINGS

These and other features, aspects, and advantages will now be described with reference to the drawings of some embodiments, which embodiments are intended to illustrate and not to limit the scope of the disclosure, and in which figures.

DETAILED DESCRIPTION

Figures 1, 8A:
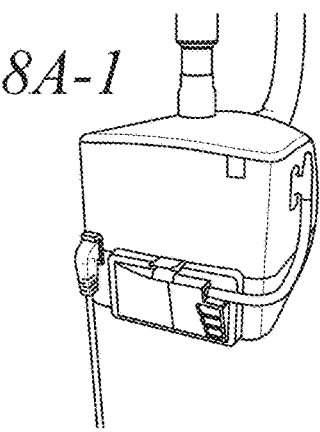
FIG. 1 is a perspective view of an apparatus that provides a humidified and heated flow of fluid to a user or patient.
FIGS. 8A-8D illustrate a series of images used in an animation showing how to replace a filter of the apparatus.
Figures 2, 8A:
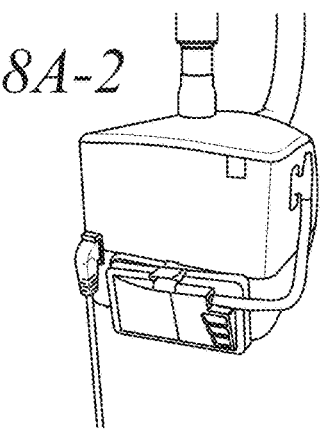
Figures 3, 8A:
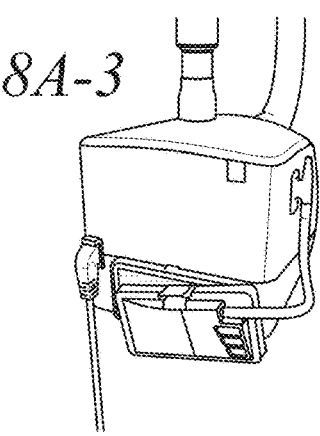
Figures 4, 8A:
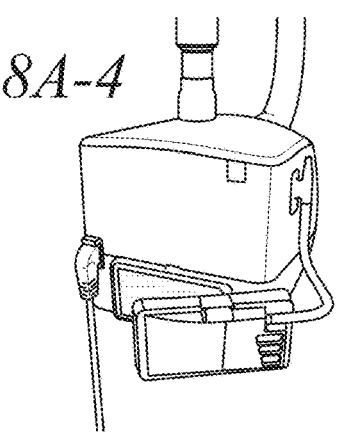
Figures 5, 8A:
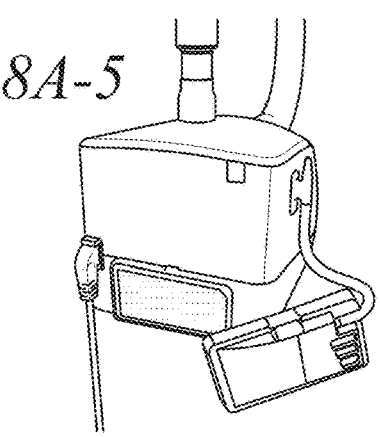
Figures 6, 8A:
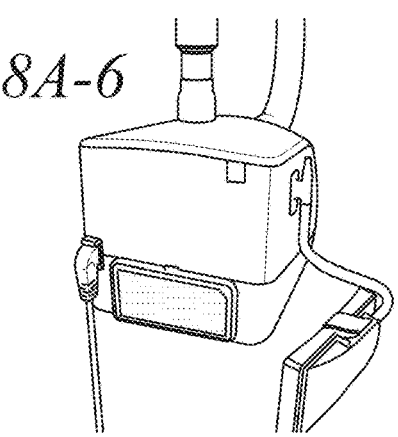
Figures 7, 8A:
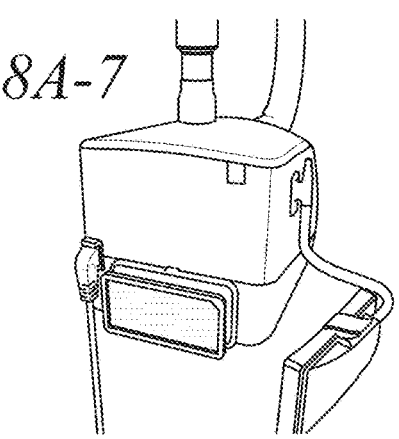
Figures 8, 8A:
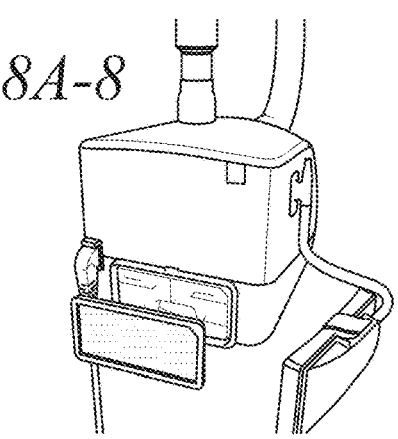
Figures 1, 8B:
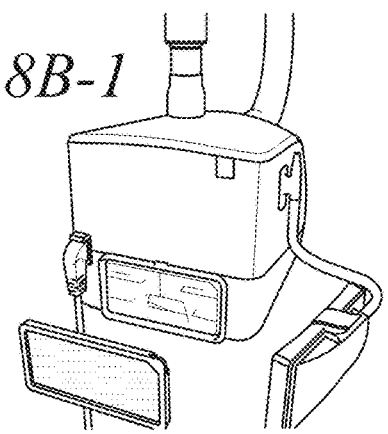
Figures 2, 8B:
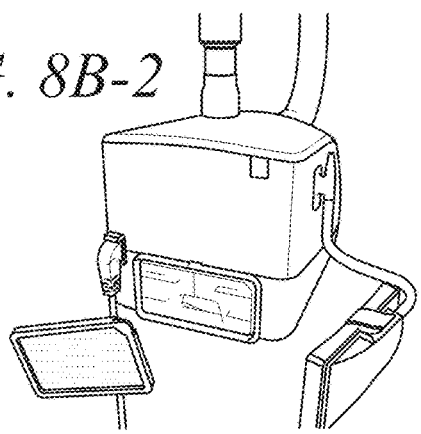
Figures 3, 8B:
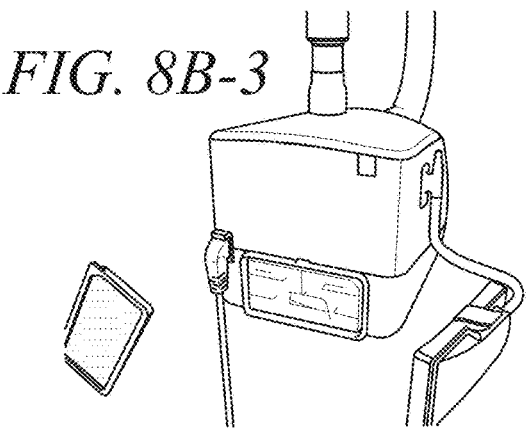
Figures 4, 8B:
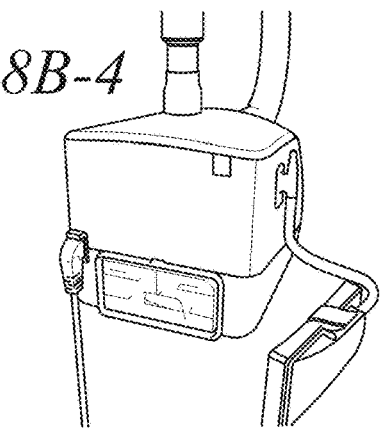
Figures 5, 8B:
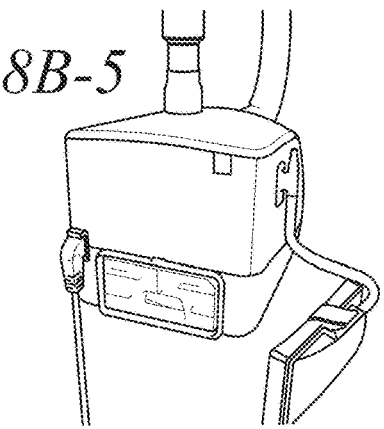
Figures 6, 8B:
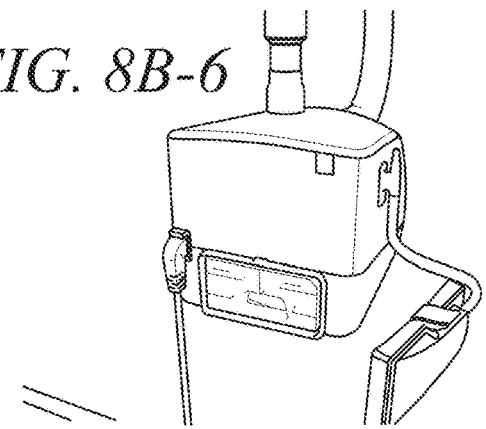
Figures 7, 8B:
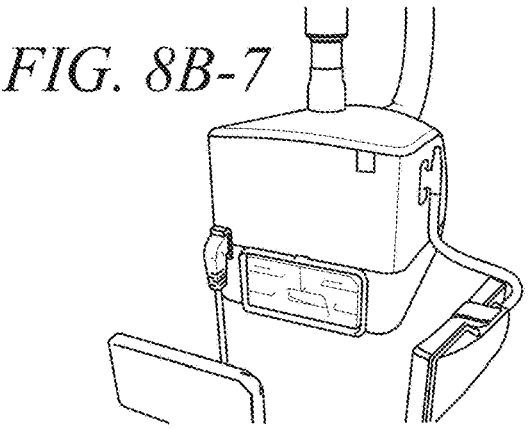
Figures 8, 8B:
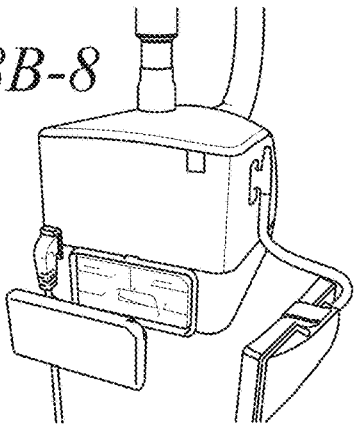
Figures 1, 8C:
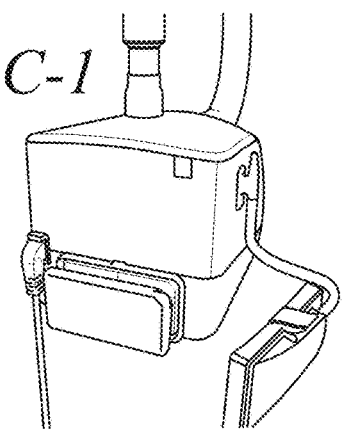
Figures 2, 8C:
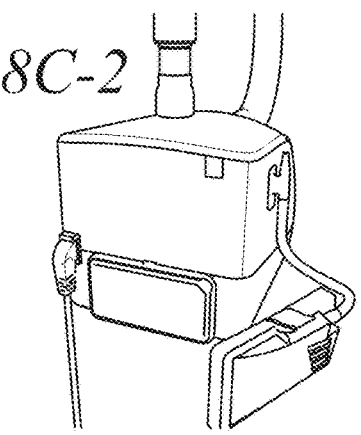
Figures 3, 8C:
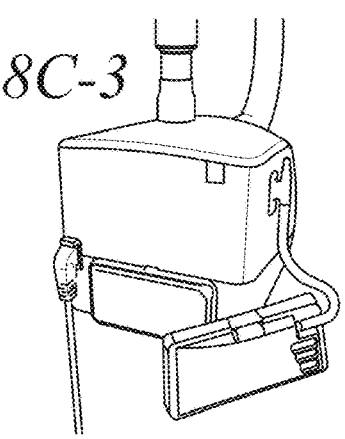
Figures 4, 8C:
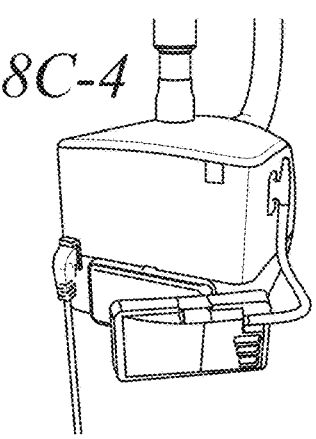
Figures 5, 8C:
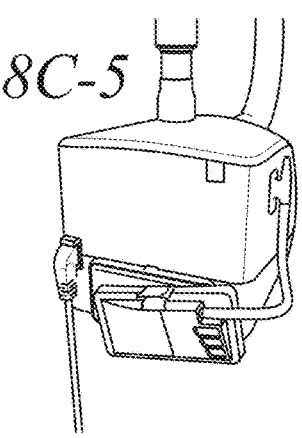
Figures 6, 8C:
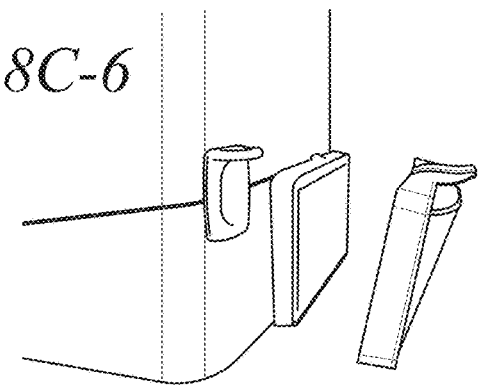
Figures 7, 8C:
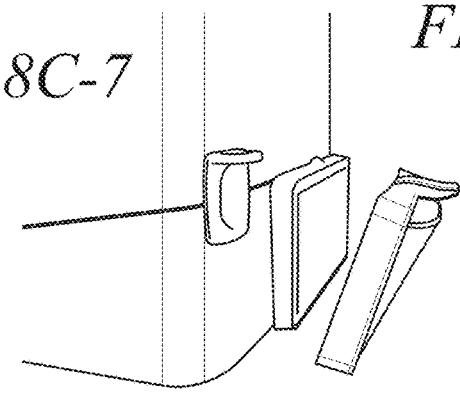
Figures 8, 8C:
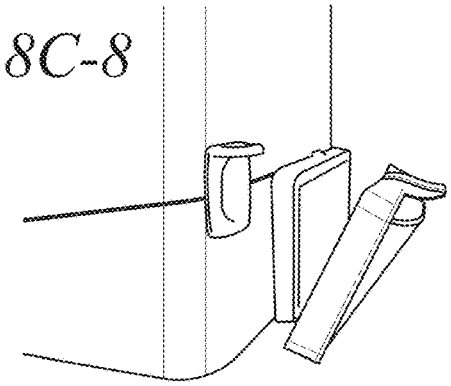
Figures 1, 8D:
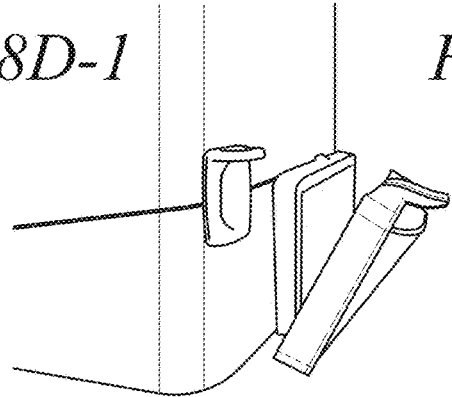
Figures 2, 8D:
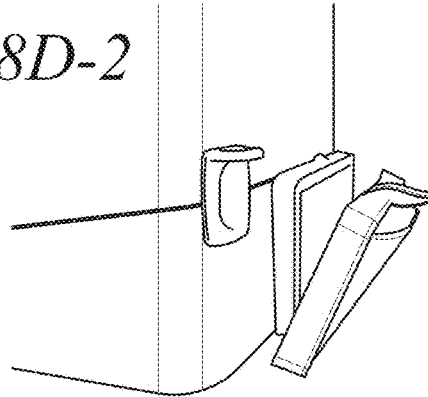
Figures 3, 8D:
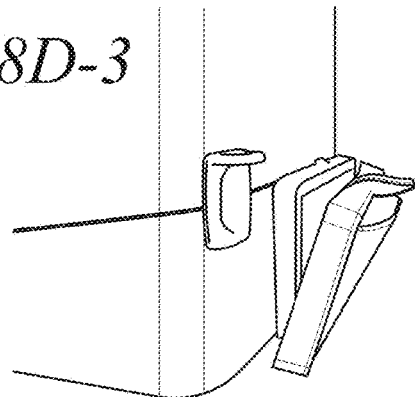
Figures 4, 8D:
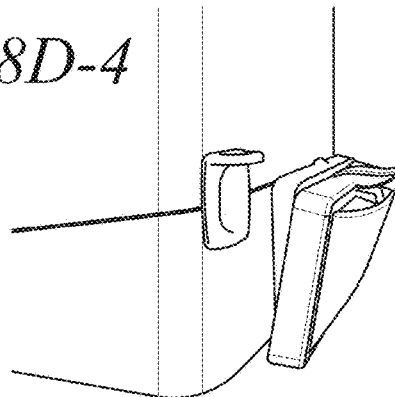
Figures 5, 8D:
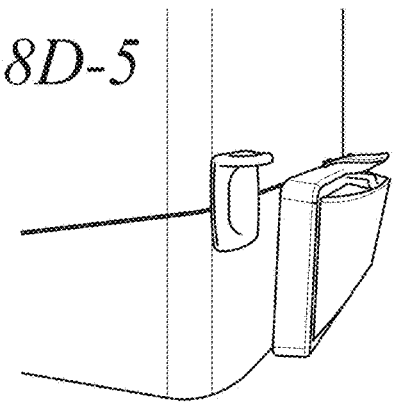
Figures 6, 8D:
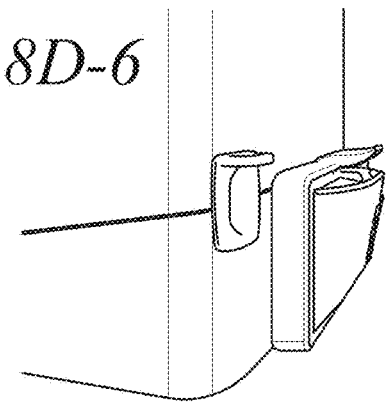

FIG. 1 illustrates an apparatus 20 that provides a humidified and heated flow of fluid to a user or patient 10. The illustrated apparatus 20 comprises a high-flow breathing assistance apparatus; however, features, aspects, and advantages of some embodiments can be used with other types of apparatus used to supply a humidified and/or heated flow of fluid (e.g., gases or air) to the user or patient 10. For example, features, aspects, and advantages of some embodiments can be used with CPAP machines, insufflation humidifiers for laparoscopic or other surgical procedures, respiratory humidifiers, humidifiers for noninvasive ventilation applications, humidifiers for invasive ventilation applications, infant resuscitation devices, and the like. The apparatus can be configured as disclosed in U.S. patent application Ser. No. 12/138,594, filed on Jun. 13, 2008, U.S. patent application Ser. No. 11/916,503, filed on Jun. 29, 2006, and/or U.S. patent application Ser. No. 10/246,328, filed on Sep. 18, 2002, each of which is hereby incorporated herein by reference in its entirety.

In some embodiments, the apparatus 20 can include a display 40 configured to display a series of images in succession that illustrate an animated action. The animated action can be used to instruct a user on how to perform a particular action. The series of images can be displayed in response to a triggering event and the animated action can be configured to present one or more methods of responding to the triggering event. The apparatus 20 can be configured to detect various triggering events and to automatically display a corresponding series of images. For example, the apparatus 20 can be configured to detect when a chamber is not correctly installed (e.g., the triggering event). In response, the apparatus 20 can display a series of images identifying the location of the problem, the element of the apparatus that triggered the event, and a method of correcting the problem (e.g., the animated action).

In some embodiments, the series of images displayed on the display 40 can include flashing lights, coloring, shading, or other similar visual cues to indicate the element or location of the triggering event. For example, if a conduit is not properly connected, the conduit can be displayed as flashing red, having a colored outline, glowing in a pulsating fashion, having an arrow pointing to the conduit, or the like. The animated action can display a method of properly connecting the conduit, after which the conduit can be displayed as flashing green, having a different colored outline, glowing in a relatively constant fashion, or the like to indicate a change from an incorrect to a correct configuration. In some embodiments, no words are used such that the visual images can communicate corrective actions to any user independent of language or technical background. In some embodiments, a user can choose to display written instructions and/or provide audible instructions in addition to the visual images. However, these written and/or audible instructions are not generally necessary because the visual images provide universal visual instructions as described herein below.

In some embodiments, the apparatus 20 can be configured to provide audible cues that correspond to the series of images presented on the display 40. For example, when an element of the apparatus 20 is illustrated as being "clicked" into place, the apparatus can emit a sound indicating that a corresponding sound should be heard when the user performs the action being illustrated. In some embodiments, the audible cue can be configured to approximate or simulate the sound a user would hear when performing the animated action. In some embodiments, the timing of the emitted sound corresponds to the timing of the animated action, such that at the time when the animated action displays the action that produces a sound, the apparatus can emit the corresponding audible cue.

With continued reference to FIG. 1, the apparatus 20 comprises a flow generating apparatus 22. The illustrated flow generating apparatus 22 can be connected to a patient interface 24 with a flexible conduit 26. The patient interface 24 can be any suitable patient interface. For example, but without limitation, the patient interface 24 can comprise noninvasive interfaces including, but not limited to, adult nasal cannula, infant nasal cannula, full face masks, combination oral/nasal masks, nasal masks, nasal pillows, high flow cannula, or the like. In some configurations, the patient interface 24 can comprise invasive or minimally invasive interfaces including, but not limited to, endotracheal tubes, insufflation devices, or the like. In some configurations, adaptors and connectors can be provided for coupling to tracheotomy devices and masks.

In the illustrated configuration, the flexible conduit 26 can comprise a heating element 30 and a sensing element 32. In some configurations, the sensing element 32 can be positioned at an end portion of the flexible conduit 26 closest to the patient interface 24. In some configurations, the sensing element 32 is positioned within the lumen defined by the flexible conduit 26 such that the sensing element 32 is exposed to the fluid being carried within the lumen. The sensing element 32 can sense a characteristic or attribute of the fluid being carried within the lumen. In some configurations, the sensing element 32 is arranged and configured to sense the temperature of the fluid passing through the lumen. In some configurations, the heating element 30 and the sensing element 32 can be arranged as described in U.S. patent application Ser. No. 12/777,370, published as U.S. Publication No. 2010/0218763 on Sep. 2, 2010, which is hereby incorporated herein by reference in its entirety.

The end of the flexible conduit 26 closest to the flow generating apparatus 22 comprises a connector 34. The connector 34 can be configured to establish both a pneumatic connection between the flow generating apparatus 22 and the lumen of the flexible conduit 26 and an electrical connection between at least the heating element 30 of the flexible conduit 26 and the flow generating apparatus 22. In some configurations, the connector 34 facilitates establishing both the pneumatic connection and the electrical connection in a single step. In some configurations, the connector 34 can be configured as disclosed in U.S. Pat. No. 6,953,354, issued on Oct. 11, 2005 and entitled "Connector for Breathing Circuits," which patent is hereby incorporated herein by reference in its entirety.

With continued reference to FIG. 1, the flow generating apparatus 22 comprises a user control interface 36. The user control interface 36 enables interaction between the user, patient 10, or another person (e.g., without limitation, health professionals, distributors, or the like) and the flow generating apparatus 22. The illustrated user control interface 36 comprises a display screen 40. The display screen 40 can be any suitable display screen. In some configurations, the display screen 40 comprises an organic light-emitting diode (OLED) screen. In some configurations, the display screen 40 can comprise a full color display with a pixel count of between about 6,000 pixels and about 500,000 pixels. In some configurations, the display screen 40 can comprise a pixel count of about 20,480 pixels. In some configurations, the display screen can comprise a screen size of about 128 pixels by about 160 pixels (vertical by horizontal). In some configurations, the display screen can be about 1.8 inches diagonally to about 4 inches diagonally. To reduce heat transferred from the screen to other components of the apparatus 22, the screen can be run with a black screen (e.g., most of the pixels are inactive during operation of the apparatus 22).

The illustrated user interface 36 comprises five different keys: a power key/button 42, a mute key/button 44, an up arrow key/button 46, a down arrow key/button 50 and a mode key/button 52. In some configurations, the user interface 36 can include some combination of mechanical keys, electro-mechanical keys, and touch-sensitive capabilities such as where the display 40 comprises a touch-screen and navigation through a menu structure or other suitable manner of device operation can be provided via the display 40. In some configurations, a joystick, a toggle, or the like can be provided for navigation through a menu structure or other suitable manner of device operation.

Figure 2:
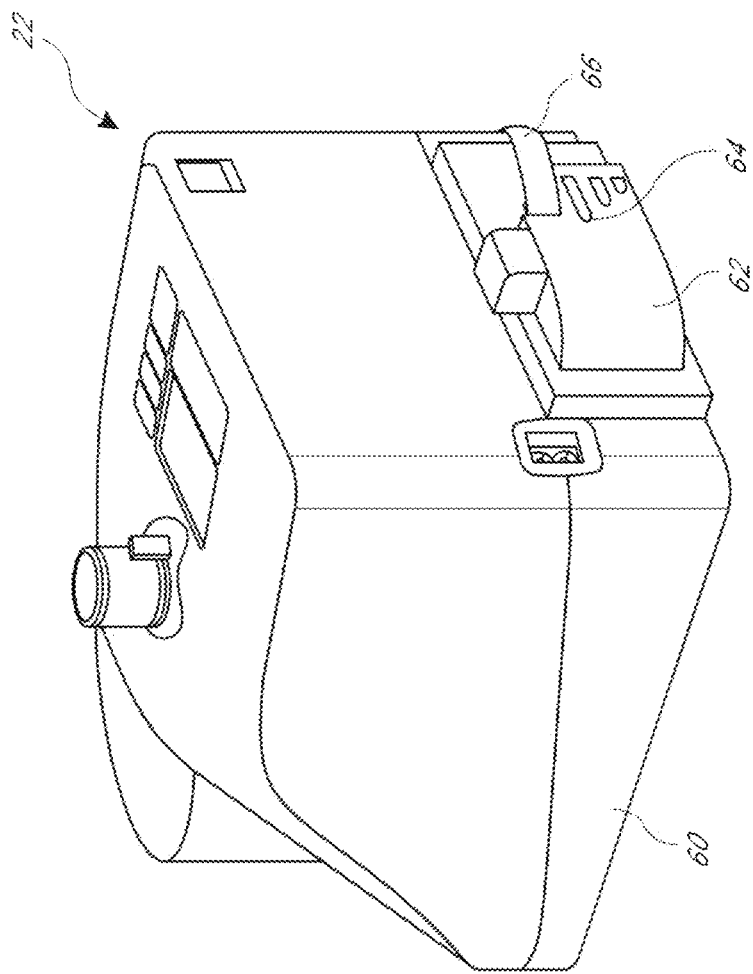
FIG. 2 is a rear perspective view of a portion of the apparatus of FIG. 1.

With reference to FIG. 2, the illustrated flow generating apparatus 22 comprises an outer housing 60. The outer housing 60 contains a flow generator (not shown). The flow generator can be any suitable component or components for generating a source of pressurized air, which generates a flow of gases through the conduit 26. As shown in FIG. 2, the housing 60 can define an inlet to the flow generator, which inlet is covered with a filter cover 62. The filter cover 62 can contain a replaceable filter element 64 that overlies the inlet to the flow generator such that it filters a flow of air that passes into the housing through openings in the filter cover 62.

With continued reference to FIG. 2, a first end of an oxygen supply conduit 66 can be connected to the filter cover 62. A second end of the oxygen supply conduit 66 can have a fitting 68 used to connect to a supply conduit from a wall supply or the like, as shown in FIG. 1. Returning to FIG. 2, the filter cover 62 or a region contained between the filter cover and the flow generator can define a mixing region for ambient air and the oxygen supplied through the conduit 66.

Figure 3:
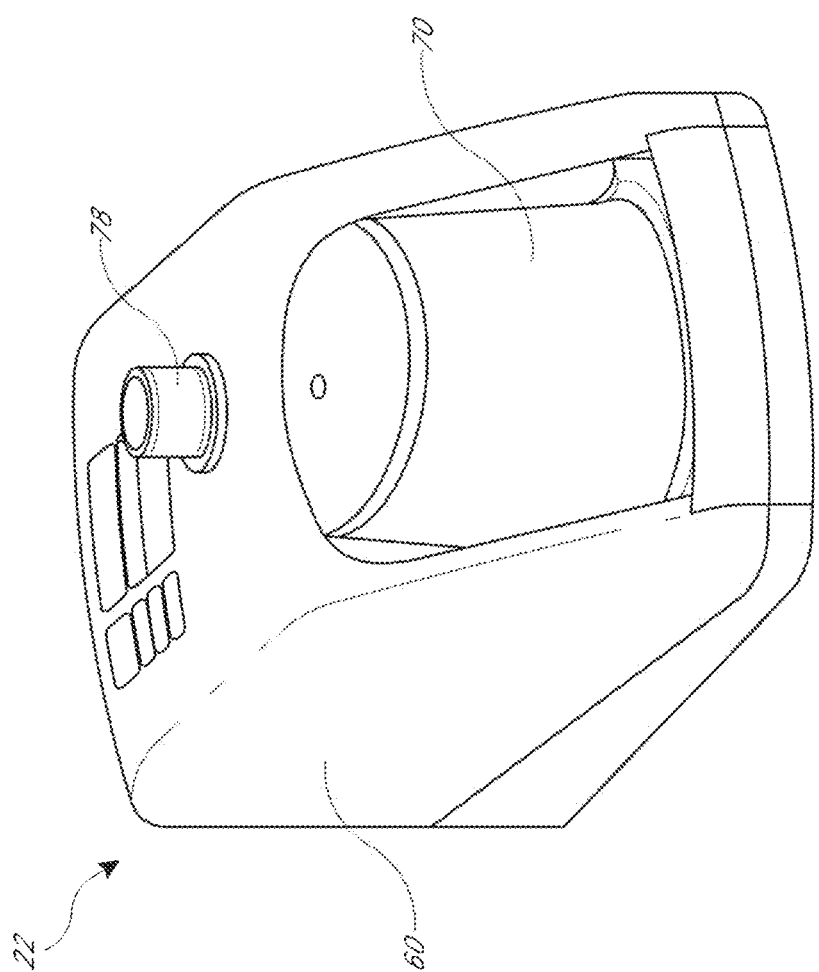
FIG. 3 is a front perspective view of the portion of FIG. 2.
Figure 4:
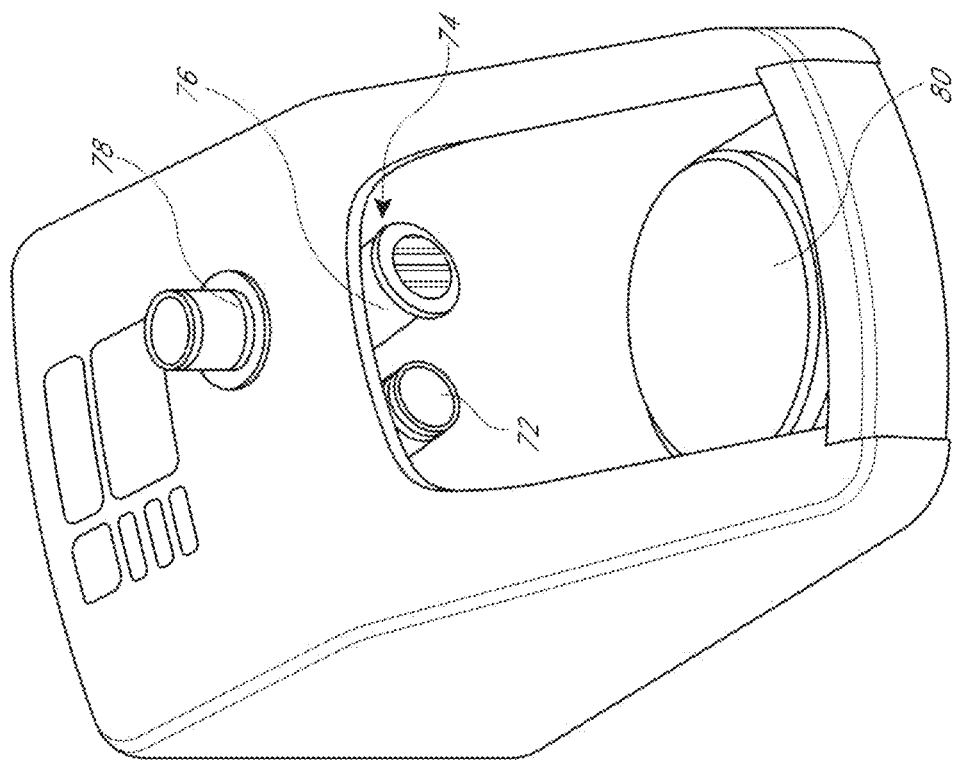
FIG. 4 is a front perspective view of the portion of FIG. 2 awaiting connection of a disinfection conduit for a disinfection mode.

With reference to FIG. 3, flow from the flow generator (not shown) passes into and through a chamber 70. An outlet port 72 (see FIG. 4) from the flow generator connects to an inlet port (not shown) of the chamber 70. A water supply can be contained within the chamber 70 such that the flow passes over the surface of the water supply to be humidified. An outlet port of the chamber 70 connects to an inlet end 74 of an elbow 76. The elbow has an outlet end 78 that connects to the conduit 26 as described above.

The chamber 70 rests atop a heater plate 80 (see FIG. 4) or other suitable heating element. The heater plate 80 can be controlled by the apparatus 22 such that the water contained within the chamber 70 can be heated to a suitable level. The water contained within the chamber 70 can be replenished from a feed set and water bag configuration, if desired.

In some configurations, the apparatus 22 can comprise one or more temperature sensors that are positioned downstream of the humidification chamber 70. In some configurations, two temperature sensors can be positioned within the elbow 76. Output from the temperature sensor in the elbow 76 and information regarding the heater plate duty cycle can be used in connection with an algorithm to detect the humidity. A system can be used such as that disclosed in U.S. Provisional Patent Application No. 61/328,521, filed on Apr. 27, 2010 and WO2009/145646, filed on May 27, 2009 and published on Dec. 3, 2009, each of which is hereby incorporated herein by reference in its entirety.

The apparatus 22 also can comprise an airflow sensor that is positioned upstream of the flow generator as well as a temperature sensor that is positioned upstream of the humidification chamber 70. In some configurations, the temperature sensor is positioned upstream of the flow generator as well. In some configurations, an oxygen sensor also can be positioned upstream of the humidification chamber or the flow generator. In some configurations, an ultrasound principle can be used to detect the oxygen content in the air based upon the detected humidity level can improve the detection of oxygen content. In some configurations, a system can be used such as that disclosed in U.S. Provisional Patent Application No. 61/620,595, filed on Apr. 5, 2012, which is hereby incorporated herein by reference in its entirety.

The apparatus 22 also comprises a suitable controller, which includes memory and other components used for sensing various characteristics of flows and operation of the apparatus. Moreover, the apparatus 22 can comprise a speaker or other audible alert generator.

Figure 5:
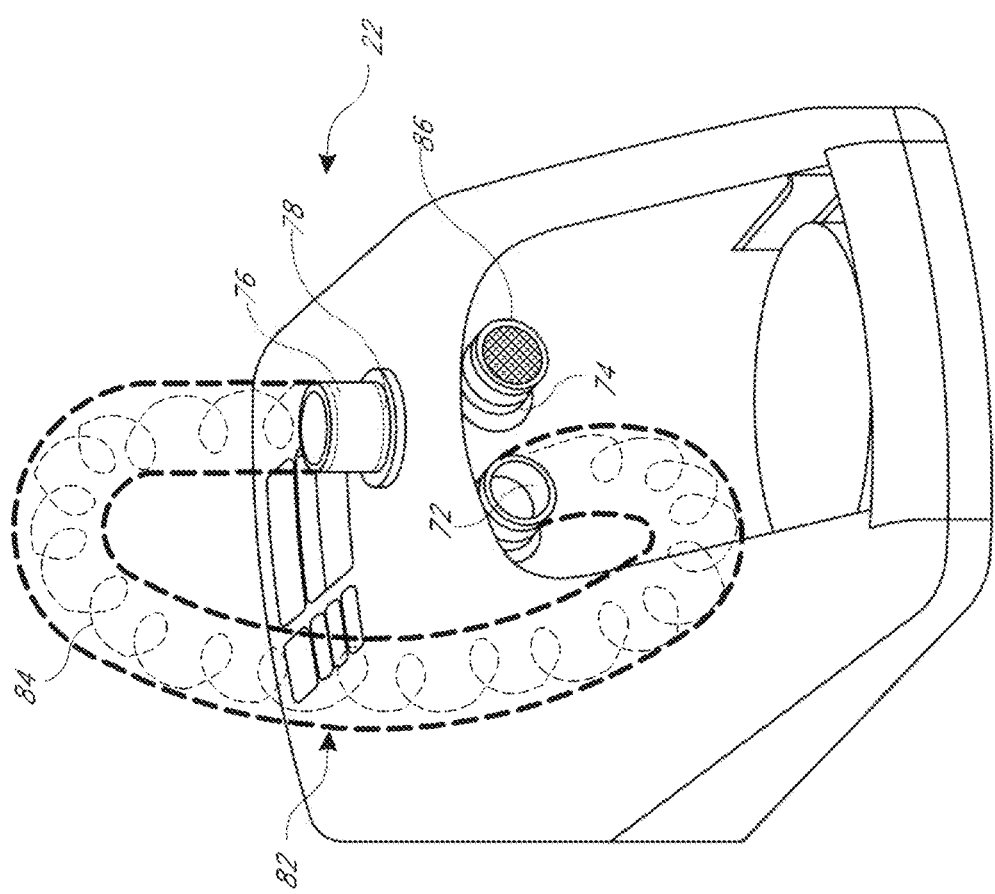
FIG. 5 illustrates the portion of FIG. 4 with the disinfection conduit connected.

With reference to FIG. 5, in order to disinfect the apparatus 22 between users, for example, a disinfection conduit 82 can be connected to the outlet 72 from the flow generator and to the outlet 78 of the elbow 76. The disinfection conduit 82 can include a heater coil 84 that is electrically connected to the electrical connection with a connector that is similar to, or the same as, the connector 34 described above. A filter cap 86 can be positioned over the inlet end 74 of the elbow 76.

Start-Up Operation

With reference now to FIGS. 6A-6D, control and operation of some features, aspects, and advantages of the illustrated apparatus 20 will be described. As will be described, the illustrated apparatus 20 can be operated in at least two main modes. In the illustrated configuration, the apparatus 20 has a primary mode that can be used in multiple-user applications and a secondary mode that can be used in single-user applications, for example but without limitation. In some configurations, the apparatus 20 can be used in the primary mode with multiple users and under generally continuous use conditions and in the secondary mode with a small number of users and under intermittent use. In other words, the apparatus 20 can be used in the primary mode in a setting such as a hospital or other healthcare facility and the same apparatus 20 can be used in the secondary mode in a setting such as a home. Such a configuration is advantageous in that a smaller number of machines need to be stocked for supply by distributors because of the ability to customize the machine to the end user.

In the description below, either the primary mode or the secondary mode may be referred to as the default mode but the apparatus 22 need not default to this mode at start up. In some configurations, the apparatus 20 comprises a disinfection mode for use between users. In some configurations, the apparatus 20 also can comprise a youth sub-mode that can be configured for use with younger users. In some configurations, the apparatus 20 can comprise a youth sub-mode for each of the primary mode and the secondary mode, which youth sub-modes can be configured for use with younger users. In some configurations, at least one of the primary mode and the secondary mode can include a conduit drying sub-mode, breathing pattern feedback sub-mode, a night-use sub-mode, and/or a transport mode. In some configurations, the secondary mode can include one or more of the conduit drying sub-mode and the night use sub-mode. Any of these modes and sub-modes, or even some other mode of operation, can be the startup mode. In some embodiments, the apparatus 20 can be configured to request an input of the desired mode or sub-mode of operation such that there is no generally pre-specified operational mode.

Figure 6A:
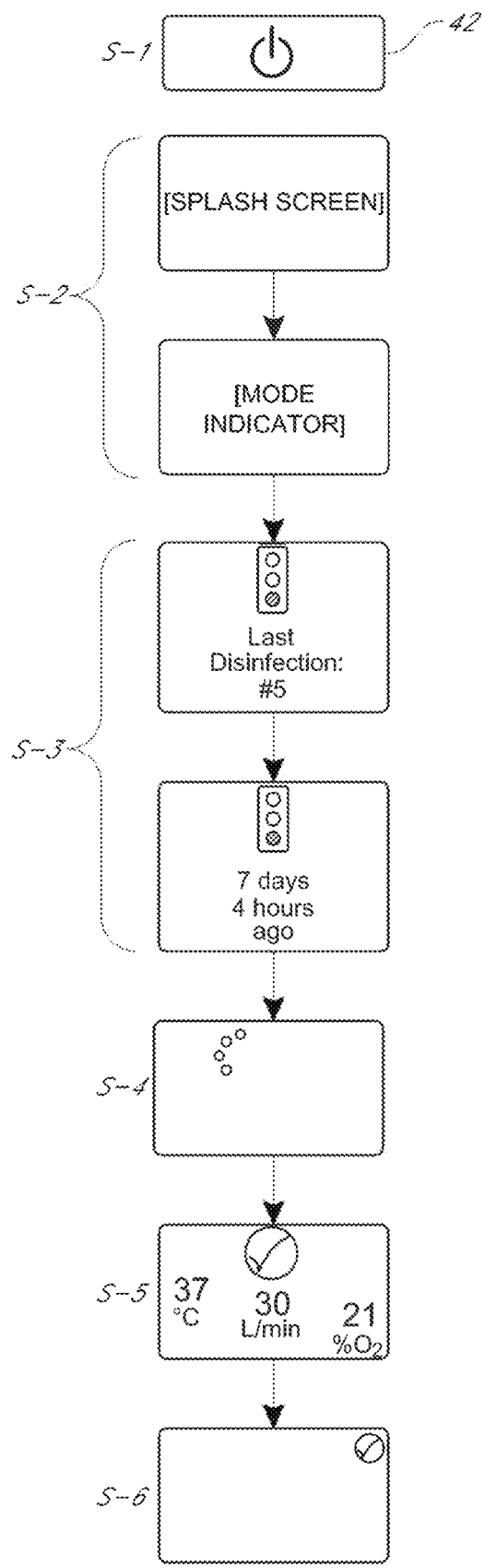
FIGS. 6A-6D illustrates a display flow for the apparatus in a primary mode.

With reference now to FIG. 6A, the apparatus 22 starts with the depression of the power button 42. See S-1. In some configurations, the power button 42 can be pressed and held for at least a minimum period of time in order to start the apparatus 22. Upon starting, one or more start screens can be presented on the screen or display 40 of the apparatus 22. See S-2. In some configurations, activation of the apparatus 22 also can be indicated audibly. For example, the apparatus 20 can include a speaker that emits a single solid tone, a series of tones, a recorded or synthesized voice, music, a chime, or other such noise or series of noises, for example but without limitation.

With continued reference to FIG. 6A, when in the primary mode or the primary mode's youth sub-mode, following the display of the start screens, the illustrated configuration presents a screen that indicates the last event. See S-3. As illustrated, if a successful disinfection was the last event, then the apparatus 22 can indicate the number of completed disinfection cycles and the time since the last disinfection cycle, for example but without limitation. Also, a graphical indicator can be presented of whether the apparatus 22 has been recently disinfected. In the illustrated embodiment, for example but without limitation, there is a green light on a traffic light. If the last event was not a successful disinfection, then a different graphical indicator can be presented (e.g., an amber light on a traffic light). In some configurations, such as the illustrated configuration, the display will alternate between the number of disinfection cycles completed and the time since the last disinfection cycle.

After a period of time, the apparatus 22 begins a warm-up procedure. In some configurations, during the warm-up procedure, the heating element 30 is energized, which heats a water supply in the chamber 70. With continued reference to FIG. 6A, a swirling icon indicates the warm-up procedure is underway. See S-4. In some configurations, the swirling icon comprises multiple stationary images that, when played in series, provide the appearance of a revolving circle animation. Other configurations also can be used to create an animation indicative of on-going warm-up. The animation, however, advantageously provides a visual indicator of on-going activity. In some embodiments, the animation can include text, sound, or some combination of images, animation, text, and/or sound.

With continued reference to FIG. 6A, once the warm-up procedure has been completed, the swirling icon (see S-4) changes to a check-mark (i.e., tick). See S-5. The completion of the warm-up procedure also can be indicated by an audible tone or range of tones (e.g., ascending scale of tones), a recorded voice or synthesized voice, a chime, a series of tones, or the like. In the illustrated configuration, the display 40 also shows a graphical depiction of values for dew point temperature, flow rate, and oxygen alarm level. This can be referred to as the main screen, the multiple value screen, or the summary screen. In some embodiments, the main screen can include additional or different information including, but not limited to, an indication of a mode or sub-mode (e.g., transport mode indicators, youth sub-mode indicators, feedback sub-mode indicators), values for other parameters, disinfection information, or the like.

Advantageously, the multiple values shown on the screen are concurrently displayed to provide a simple review of these values. The readings can advantageously be displayed in other than a straight line to improve readability. In other words, to aid reading, one or more of the multiple values are offset relative to the others of the multiple values. For example but without limitation, in the illustrated configuration (see S-5), the temperature is illustrated higher on the screen than the flow rate and the flow rate is illustrated higher on the screen than the oxygen alarm level. The display also can be provided with a screen saver (see S-6) that displays after a set period of display inactivity. In some embodiments, the screen saver can include additional information, animations, or the like.

The menus and display screens of the apparatus 22 can advantageously be configured to be graphics-based instead of, or in addition to, being text-based. By displaying information, options, menus, instructions, and the like in a graphical manner, the display can be utilized in situations where different languages are spoken and/or where multiple languages are spoken. This can reduce or eliminate a need to translate instructions or information when the apparatus is used in various locations. This can also reduce or eliminate misunderstandings or mistakes that occur due to language differences or inaccurate translations of text-based information.

Mode Selection and High Level Settings

Figure 6B:
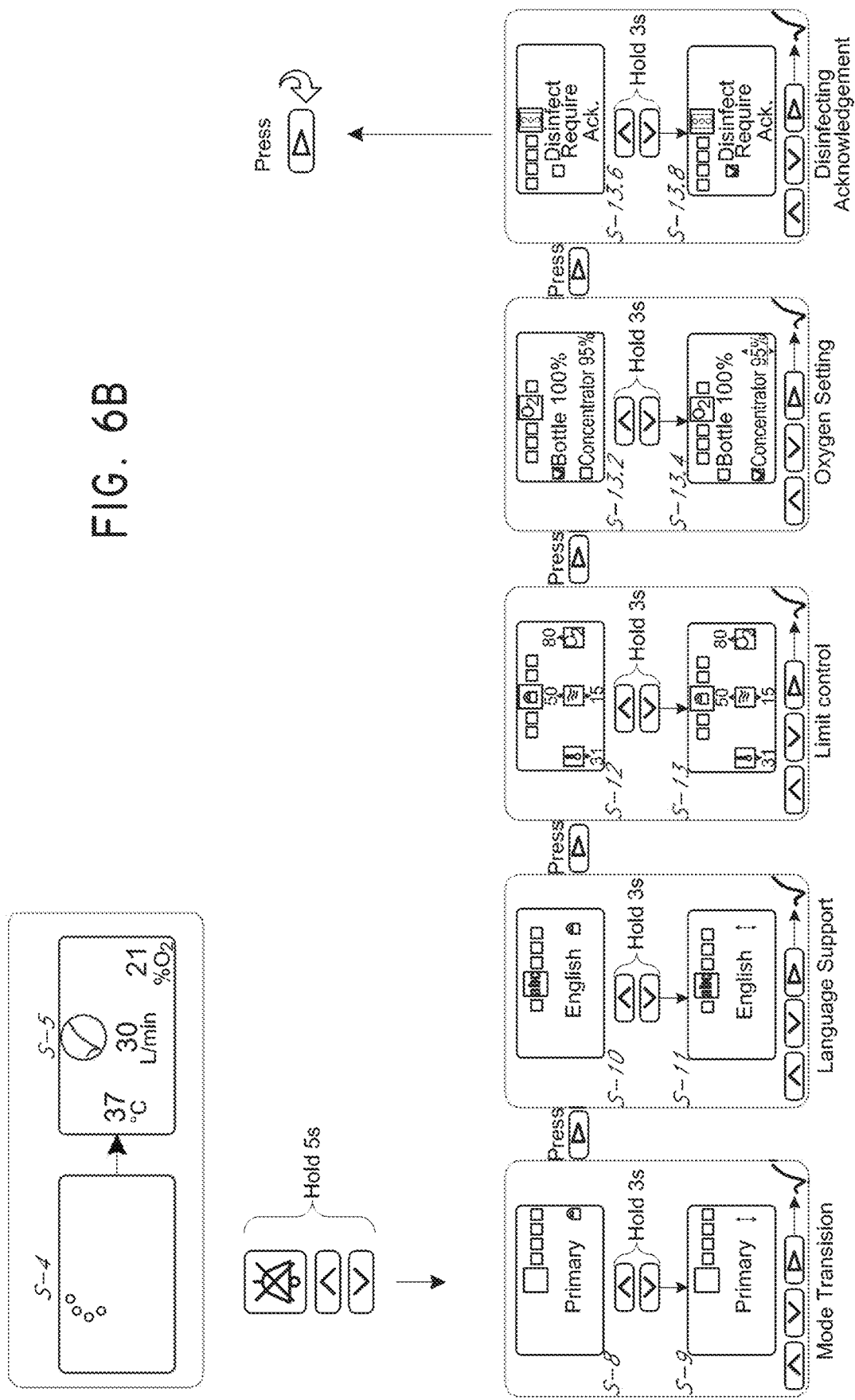

With reference to FIG. 6B, from the main screen (see S-5) a key combination can be used to enter a top-level control menu, until ready to use. See S-7. In the illustrated configuration, the key combination comprises pressing the top three buttons (e.g., mute key 44, up arrow key 46, down arrow key 50) for at least a minimum period of time. In some configurations, the minimum period of time is 10 seconds. Other key combinations and minimum periods of time can be used.

In the illustrated configuration, the top-level control mode is accessible in the default mode (e.g., the primary mode or the secondary mode). The top-level control menu is used by individuals other than the user or patient 10. For example, the top-level control menu can be used by someone other than the ultimate user/patient 10 or the healthcare provider. In some configurations, the top-level control menu can be used by individuals authorized by the owner, distributor, or manufacture of the apparatus 22 such that various set points can be established for the owner that are not available for use by the user (e.g., the user 10 is unaware of the top-level control menu and/or the key combination used to access the top-level control menu).

Upon entry into the top-level control menu, the illustrated apparatus 22 enters a mode adjustment screen. See S-8. The mode adjustment screen allows changing between the primary mode and the secondary mode. The mode adjustment screen presents information regarding the current mode (e.g., primary mode ("Primary"), secondary mode ("Secondary"), etc.).

While the mode adjustment screen is presented (see S-8), pressing and holding the up and down arrow keys together for a preset period of time unlocks the mode for adjustment. See S-9. The up arrow key 46 and the down arrow key 50 enable changing between available modes. Once a mode has been selected, pressing the mode button 52 reboots the machine in the selected mode. In some embodiments, the apparatus 22 only reboots when the selected mode is different from the previous mode.

In the illustrated configuration, while in the mode adjustment screen (see S-8), pressing the mode button 52 activates a language adjustment screen. See S-10. While the language adjustment screen is presented, pressing and holding the up arrow key 46 and the down arrow key 50 together for at least a minimum period of time unlocks the language adjustment selection. See S-11. The up arrow key 46 and the down arrow key 50 enable changing between languages. Once a language has been identified, pressing the mode button 52 confirms the identified language setting.

In the illustrated configuration, while in the language adjustment screen (see S-10), pressing the mode button 52 activates a target limit adjustment screen. See S-12. While the target limit adjustment screen is presented, pressing and holding the up arrow key 46 and the down arrow key 50 together for at least a minimum period of time unlocks the target limit adjustment. See S-13. In the target limit adjustment screen, the limits (e.g., lower limit and upper limit) between which target values can be set will be adjustable. Thus, if an owner or provider of the apparatus 22 desires that the flow target be selected from within a range between 15 L/min and 30 L/min at all times, those values can be set using the target limit adjustment screen.

While any of a number of parameters can be monitored and/or adjusted, the illustrated embodiment demonstrates monitoring, using, setting and/or adjusting the dew point temperature, the flow rate, the oxygen level, the oxygen setting, and the disinfection setting, for example but without limitation. In the illustrated configuration, the oxygen level is merely detected and is not adjusted by the apparatus 22. In some embodiments, the values defining the range are locked and, when in the target limit adjustment screen (see S-12), depressing the up arrow key 46 and the down arrow key 50 together for a set period of time can unlock the values for adjustment. The unlocking of the values can be audibly indicated through the speaker (e.g., a solid tone, series of tones, music, chime, click, or the like).

With continued reference to FIG. 6B, in the illustrated configuration, the lower limit for the temperature range can be adjusted while the upper limit is not adjustable. In some configurations, the upper limit is about 37 C. The lower limit, in the illustrated configuration can be about 31 C. In some configurations, the temperature can be adjusted in increments of 3 C and, as such, the lower limit temperature can be set to 31 C, 34 C or 37 C. In the illustrated configuration, both the upper limit and the lower limit of the flow rate range can be adjusted. The flow range can be adjusted in 5 L/min increments between about 50 and about 15. In the illustrated configuration, the oxygen alarm level can be adjusted in 5% increments between about 90 and about 0. In some configurations, there is no lower limit for the oxygen alarm level. The oxygen alarm level does not change the level of oxygen supplied but is used to provide an alarm if the level of oxygen being supplied is outside of a specified level.

In the illustrated configuration, the oxygen setting can be used to indicate whether the oxygen source is 100% bottle oxygen or a lower fraction from a concentrator which also has an argon content, for example. See S-13.2. The oxygen concentration can be set and can range between about 20% and about 100%. Typically, the oxygen concentration can range between about 90% and about 95%. Pressing the up and down buttons allows the user to select the oxygen source and/or to adjust the oxygen concentration. Pressing the mode button can lock-in or confirm the selection and/or toggle the selection of the oxygen source. See S-13.4.

With continued reference to FIG. 6B, the disinfection setting can be used to require a user to acknowledge a disinfection warning (e.g., by pressing the mode button 52) when the apparatus is being restarted in a defined disinfection state. See S-13.6. For example, when an apparatus is turned on without being disinfected prior to being shut off the last time it was in use, an amber or orange indicator light can be displayed during startup. If disinfection acknowledgement is selected, the user will be required to acknowledge the warning by pressing the mode button 52 when the indicator is displayed before resuming normal operation or startup. This can be set to force an acknowledgement on the part of the person operating the apparatus 22 that no disinfection mode has been run on the apparatus 22 since it was last used. In other words, the person operating the apparatus must consciously depress the mode button 52 to acknowledge this information. Using the up and down arrows can alternatively select and deselect this setting. Pressing the mode button confirms the selection. See S-13.8.

In some embodiments, the person changing the settings is alerted to the value being changed by a visual indicator. In the illustrated configuration, the number being adjusted changes between a colored number and a white number. In this manner, the number being adjusted appears to be pulsating or blinking. For example, as the user uses the mode button 52 to cycle from "temperature lower limit" to "flow lower limit" to "flow upper limit" to "oxygen alarm upper limit," the number being adjusted has the appearance of blinking due to being displayed in more than one color in succession.

In some embodiments, pressing the mode button allows the user to cycle through the settings screens. When adjustments have been made, the apparatus 22 reverts to the swirling icon (see S-4) or the summary screen (see S-5) after an inactivity period has elapsed or after a particular key combination is pressed (e.g., holding down the mute, up, and down buttons for at least a minimum period of time).

Value Level Settings

As discussed above, on the main multiple value screen (see S-5) of the illustrated embodiment, the display screen 40 can illustrate current dew point temperature, current flow rate and current oxygen level, for example but without limitation. These values are based upon real time readings. In some embodiments, the readings are made during warm up as well as during use. During any changes to the readings (e.g., until set points have been reached), the numbers flash between a white illustration and a colored illustration to provide a visual pulsing effect such as that described above. Once a set point value (e.g., the target value) has been obtained, the number will go solid.

Figure 6C:
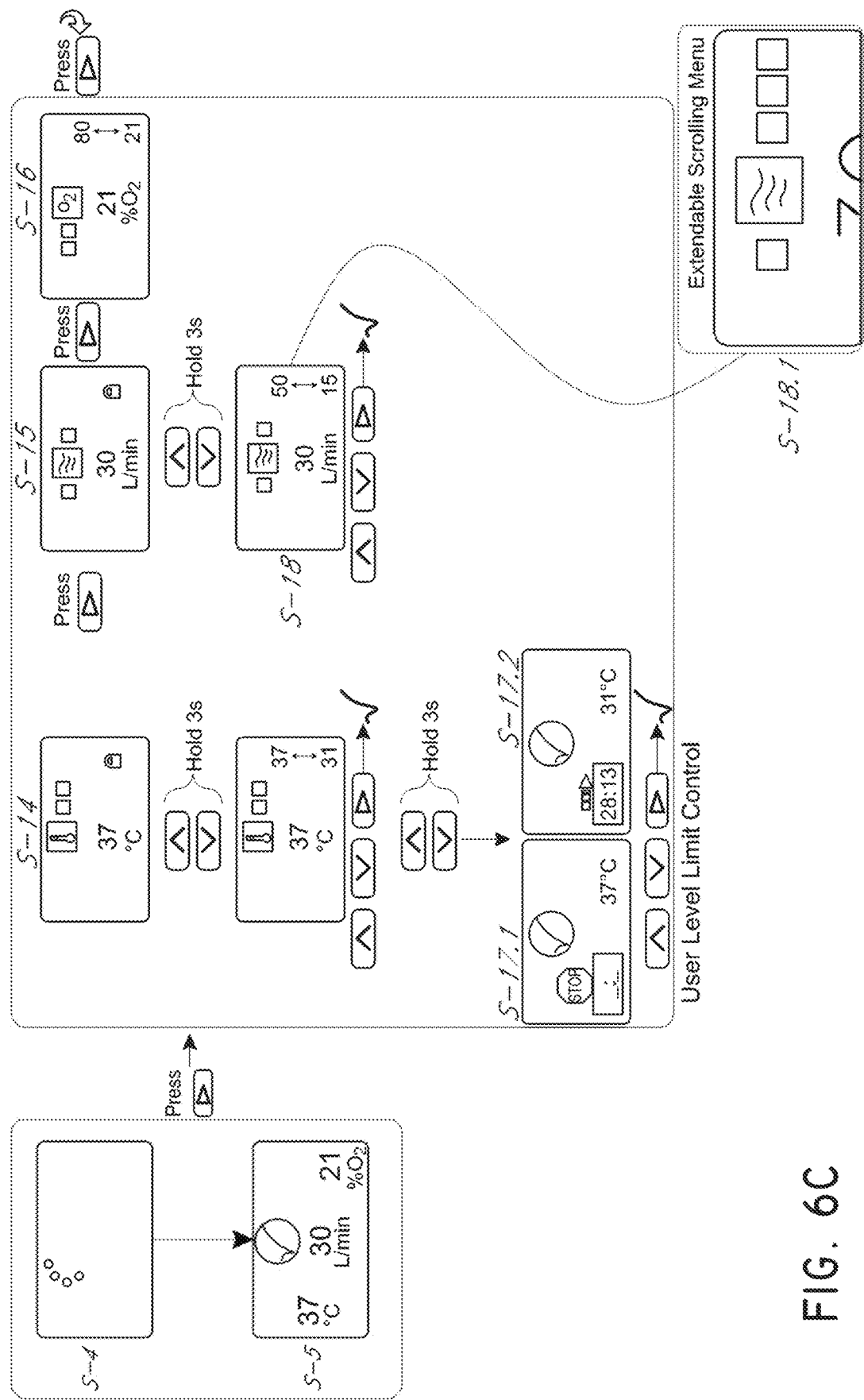

With reference to FIG. 6C, in any mode, when not on the main screen (e.g., when on the temperature target screen and/or the flow target screen), depressing the mode button will cycle among a plurality of values. The values can be represented by smaller icons or other shapes that, when selected, increase in size and possibly detail. The plurality of smaller icons or other shapes facilitate an expandable scrolling menu that allows a large number of values to be displayed even on a smaller display screen 40. See S-18.1. While the illustrated configuration depicts a temperature target screen (S-14), a flow rate target screen (S-15) and an oxygen level alarm target screen (S-16), any number of additional screens can be presented. For example, the apparatus 22 can display a day/night sub-mode screen, a transport mode screen, or the like. Each of these screens can be used to select a value within the preset range (e.g., the range specified in S-12 and S13). In some configurations, a default setting for the dew point temperature target is 37 C.

In any mode, when not on the main screen, depressing the up and down arrows together for at least a minimum period of time will allow the user to adjust the temperature target (S-17) and/or the flow rate target (S-18). In some configurations, these values are locked and depressing the up arrow key 46 and the down arrow key 50 at the same time for at least a minimum period of time can unlock the values. The unlocking of the values for adjustment can be audibly indicated (e.g., a solid tone, series of tones, click, voice, music, chimes, etc.).

Once unlocked, the values for the target temperature and the target flow rate can be adjusted within the preset range of values using the up arrow key and the down arrow key. See S-17 and S-18. For example, in some configurations, the dew point temperature can be adjusted between 31 C and 37 C. For example, 31 C might be used if delivery of the flow is through a mask, while 37 C might be used where upper airway is bypassed (e.g., tracheotomy) and 34 C might be used for a small, petite patient receiving nasal gas delivery. By way of further example, the flow rate may be adjusted within a range of about 15 L/min. and 50 L/min. While not illustrated, the oxygen level at which the apparatus will alarm can be adjusted within a range of 20% and 90% (i.e., any adjustment of oxygen levels will be made at the wall valve or another valve).

When on the temperature adjustment screen, pressing the mode button 52 for at least a minimum period of time (e.g., at least about 5 seconds) can display the transport mode screens. See S-17.1 and S-17.2. The up and down arrows can be used to alternate between selecting the normal mode or the transport mode. Pressing the mode button again confirms the selection. In the transport mode, the temperature setting for the heater plate can be reduced (e.g., typically to about 31 C from about 37 C in the normal mode). In some embodiments, entering the transport mode can cause the apparatus 22 to reduce or minimize power usage by the heater plate 80, motors, and the like. The reduction or minimization of power can be done to reduce power consumption when connected to a universal power supply ("UPS") for transportation from one location to another when the apparatus cannot or will not be plugged into an electrical socket. When in transport mode, the apparatus 22 can have a countdown timer with a preset period of time (e.g., about 30 minutes), after the expiration of which the apparatus 22 automatically reverts to a normal mode of operation. The screen can display the temperature setting and the countdown timer indicating when the apparatus will automatically revert to a normal mode of operation. In some embodiments, the countdown timer can be reset by the user if the transportation will last longer than the timer provides. In some embodiments, the apparatus reverts to the mode of operation it was in prior to being put into the transportation mode. In some embodiments, the transportation mode screen (S-17.2) can display other information or indicators, such as a flow rate, an oxygen setting, a youth-sub mode, or the like.

In some embodiments, the apparatus 22 can be configured to enter transport mode when connected to a UPS. The apparatus 22 can be configured to understand and communicate appropriate handshake protocols with UPS systems so as to recognize when it is connected to a UPS rather than an electrical wall socket. In some embodiments, the apparatus 22 can remain in transport mode until disconnected from the UPS and/or connected to an electrical wall socket.

Following adjustment, the selected value will be locked after a set period of time (e.g., five or seven seconds) or when the mode button 52 is pressed to move to the next screen. After a preset period of time, when adjustments have been made, the apparatus 22 reverts to the swirling icon (see S-4) or the summary screen (see S-5) after an inactivity period has elapsed or when a defined key combination has been pressed.

Youth Sub-mode

Figure 6D:
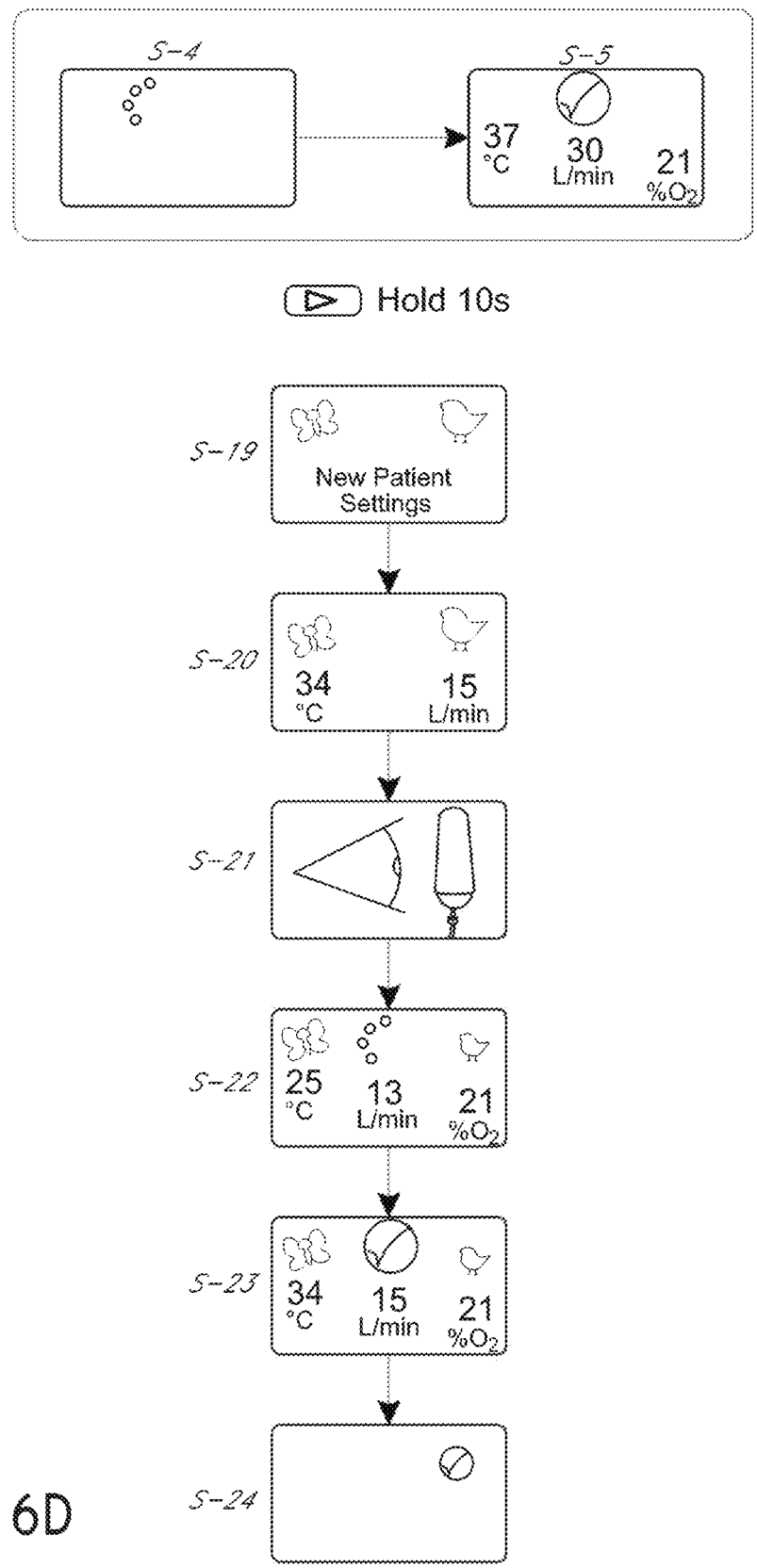

In either the primary mode or the secondary mode, at any time during warm-up (see S-4) or after the apparatus is ready for use and when the main screen is visible (see S-5), the apparatus 22 enters a youth sub-mode when the mode button 52 is pressed for at least a minimum period of time (e.g., about 10 seconds), as illustrated in FIG. 6D. After each disinfection, which should be performed after use and prior to a subsequent patient/user, the apparatus 22 can be configured to require depression of the mode button 52 to enter the youth sub-mode. This forces an acknowledgement on the part of the person operating the apparatus 22 that the settings have changed. In other words, the person operating the apparatus must consciously depress and hold the mode button 52.

Upon entry into the youth sub-mode, one or more entrance screen can be provided. See S-19. At least one entrance screen, in some embodiments, is distinct from the default mode entrance screen. In the illustrated configuration, attention-getting animations are provided on the youth sub-mode entrance screen. The animations in the illustrated configuration are a butterfly and a bird. The butterfly and the bird move onto the screen. In some configurations, the butterfly and the bird can move inward from the edges of the screen to attract attention.

The apparatus 22, when first entering the youth sub-mode, can adjust the target temperature and/or the target flow rate. In some configurations, the target temperature is adjusted to a level lower than the level available in the default (e.g., primary or secondary) mode, which was discussed above. In some configurations, the target temperature in the youth sub-mode is about 34 C. The target flow rate can be set to the flow rate closest to the prior setting in the default (e.g., primary or secondary) mode. If the prior flow was above the youth sub-mode range, then the highest flow in the range will be selected. If the prior flow was within the youth sub-mode range, then the prior flow will be used. In some configurations, if the target flow rate set in the default (e.g., primary or secondary) mode is above about 20 L/min, the target flow rate will adjust to 20 L/min in the youth sub-mode. If the apparatus 22 has been used in the youth sub-mode previously, the apparatus 22 will recall the settings from the prior use in the youth sub-mode and set the targets according to the prior settings. See S-20.

An additional animation (e.g., an eye and water bag) also can be provided to remind the person operating the apparatus 22 that the water supply should be monitored because there may be no water out alarm in the youth sub-mode. See S-21. Because the youth sub-mode involves lower flow rates, the rate of evaporation is slower than at higher flow rates. Because there may be no humidity sensor, detection of low water conditions can be based upon a comparison of the energy required to operate with a full chamber and the energy required to run with no water in the chamber. In the default (e.g., primary or secondary) mode, if the current state is trending toward no water, then an alarm is issued. At low flow rates, the difference may be not large enough to detect reliably. The detection is based upon the duty cycle applied to the heater plate. Because less water is evaporated at low flow rates, the change may be too subtle to reliably and repeatably detect.

Following the depiction of the animations, the new target settings will be presented. See S-22. In addition, the swirling icon discussed above can be presented to demonstrate visually that the apparatus 22 is still warming up. Upon completion of the warm up, the swirling icon can be replaced with a check-mark (i.e., tick). See S-23. As discussed above, after a period of inactivity, a screen saver mode can be entered. See S-24.

Feedback Sub-mode

In any of the primary mode, the secondary mode, or the associated youth sub-modes, the apparatus 22 can comprise a feedback sub-mode. The feedback sub-mode can be selected by the user or can be automatically selected by the apparatus. For example, if a detected breathing rate exceeds a predetermined breathing rate, the apparatus can enter the feedback sub-mode to assist the user in attaining a desired breathing pattern or breathing rate. The feedback sub-mode can provide visual and/or audible cues to coach a patient/user to obtain the desired breathing pattern or breathing rate.

Disinfection Mode

After shutdown, the disinfection conduit 82 can be connected to the apparatus 22. On one end, the disinfection conduit 82 has the same connector as the patient conduit 26. On the other end, the disinfection conduit 82 is sized and configured to mate to the outlet 72 from the flow generator. The heater wire 84 with the same resistance as the heater wire 30 in the patient conduit 26 can be installed within the disinfection conduit 82. In some embodiments, the disinfection conduit 82 does not include a temperature sensor. The disinfection conduit 82 can be coaxial in construction with an insulating sleeve surrounding the conduit that defines the flow path such that insulating air can be trapped between the inner conduit and the outer sleeve.

The filter cap 86 can be joined to the end of the disinfection conduit 82 opposite to the connector with the heater wire connection. The cap 86 can be joined by a strap to the disinfection conduit 82 to reduce the likelihood of the cap 86 being lost between uses. During disinfection, the cap 86 can be installed over the inlet 74 to the elbow 76, as will be described below.

In some embodiments, the elbow 76 is mechanically cleaned (e.g., bottle brush) and chemically cleaned before the disinfection conduit 82 is connected to the elbow 76. The disinfection conduit 82 is connected to the outlet of the flow generator and the outlet 72 of the elbow 76 such that flow through the elbow 76 is reversed relative to the norm.

The cap 86 can be installed over the other end of the elbow 76. The cap 86 is secured with an outer sleeve that overlaps an outer surface of the port. The cap comprises a filter medium and a protruding member. The protruding member reduces the likelihood of the cap being installed on the outlet from the flow generator because the protruding member contacts a non-return valve positioned within the outlet from the pressurized air source. The protruding member also decreases the size of the flow path to increase the velocity of the airflow through a non-heated region disposed between the end of the heated disinfection conduit 82 and the discharge point of the filter cap 86. In addition, the rapid expansion of the higher speed airflow as it exits the cap 86 causes a rapid decrease in temperature of the air. Thus, there is a high disinfection temperature right up until the discharge point of the filter cap 86, following which the temperature drops dramatically.

Figure 7:
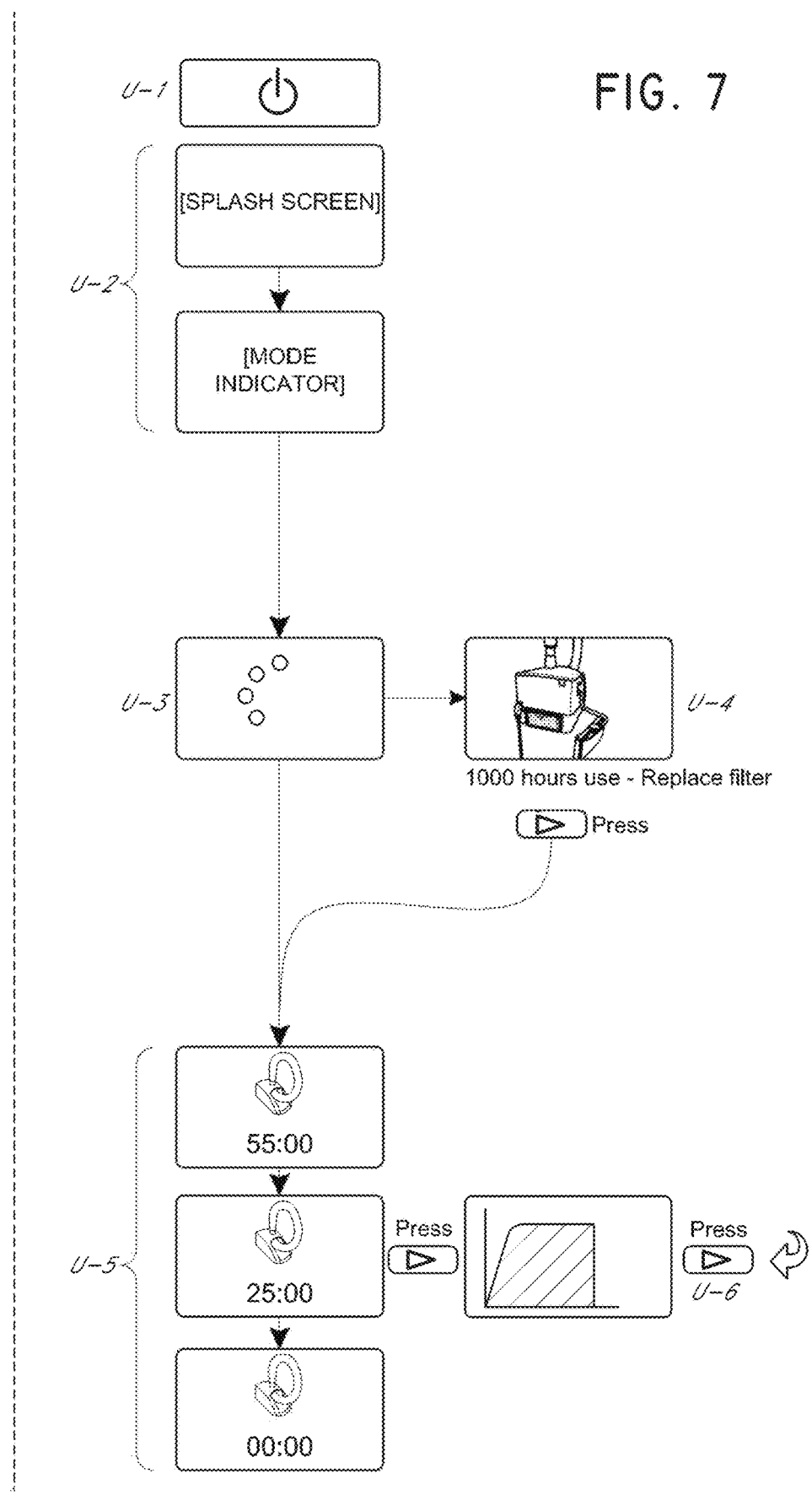
FIG. 7 illustrates a disinfection mode display flow for the apparatus.

With reference to FIG. 7, with disinfection conduit 82 installed, the apparatus 22 is turned on by pressing the power key 42. See U-1. The system detects the disinfection conduit 82 because the temperature sensor is not included in the disinfection conduit 82 but the resistance of the heater wire 84 is detected. Because of the detection of the presence of the disinfection conduit 82, the disinfection mode begins and start screens are provided to the display 40. See U-2. Other manners of starting the disinfection mode also can be used.

The display then presents a swirling icon similar to that described above to indicate that the apparatus 22 is warming up. See U-3. In some embodiments, the swirling icon has a different color to indicate that the apparatus 22 is warming up for disinfection mode instead of normal operation. In some configurations, other animations or indicators can be used.

The apparatus 22 monitors usage conditions and, when a target usage limit has been reached, the apparatus 22 provides a suggestion to replace the inlet air filter. See U-4. As shown in FIGS. 8A-8D, in the illustrated configuration, the apparatus 22 presents an animation illustrating removal and replacement of the air filter. The animation presents the cover being removed, the old filter being removed, the new filter being inserted and the cover being replaced. The animation can comprise a plurality of frames that show slight movement from one frame to the next such that presenting the frames in series provides a visual animation. In some embodiments, a portion of the image sequence presents a "zoomed-in" display of a portion of the apparatus, such as the filter cover in FIG. 8C. This may be advantageous to show detailed visual information and/or to present detailed visual information on a relatively small display or a display with relatively few pixels (e.g., a display with a relatively low resolution). In some embodiments, the apparatus 22 can be configured to produce an audible cue or sound at the time in the animation when the filter cover is shown as being closed, the audible cue being used to indicate that a sound should be produced when the filter cover is correctly closed. Other animations and/or audible cues can be used.

Returning to FIG. 7, the apparatus 22 can be configured to request an acknowledgment of an indication to replace the filter. In the illustrated configuration, the apparatus 22 requests pressing of the mode button 52 in order to proceed with disinfection. Accordingly, the suggestion to replace the air filter is acknowledged through the pressing of the mode button 52.

As discussed above, during start-up, a colored swirling icon can be used. See U-3. Following start-up, the system monitors temperature in the elbow 76 to detect whether the temperature is rising fast enough in accordance with a disinfection mode. Because the disinfection conduit 82 has a heater 84 and because the airflow is being heated by the heater 84 prior to delivery to the sensor in the elbow 76, the temperature profile varies relative to having a breathing conduit 26 with a heater 30 positioned after the elbow 76 and a chamber 70 positioned before the elbow 76.

During the disinfection process, a counter is used to show progress. See U-5. The counter can count down the amount of time remaining in the disinfection mode. Pressing the mode button 52 will present a graphical display that updates to show progress of the disinfection. See U-6. The graphical display can be temperature over time and a colored bar can be presented to graphically depict the amount of time over a set temperature (e.g., 90 C). In some embodiments, this is a display that dynamically updates as the disinfection cycle progresses. At the end of the disinfection cycle, the display alternates between announcing a successful completion and the total number of successful disinfections. In some embodiments, announcing the successful completion can comprise displaying visual information, emitting a sound, or some combination of both visual and audible cues.

Secondary Mode

Figure 9A:
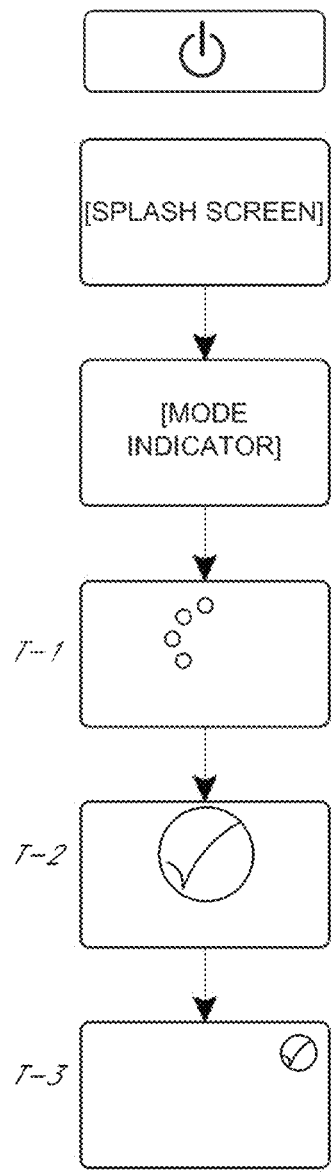
FIGS. 9A-9C illustrate another display flow for the apparatus in a secondary mode.
Figure 9B:
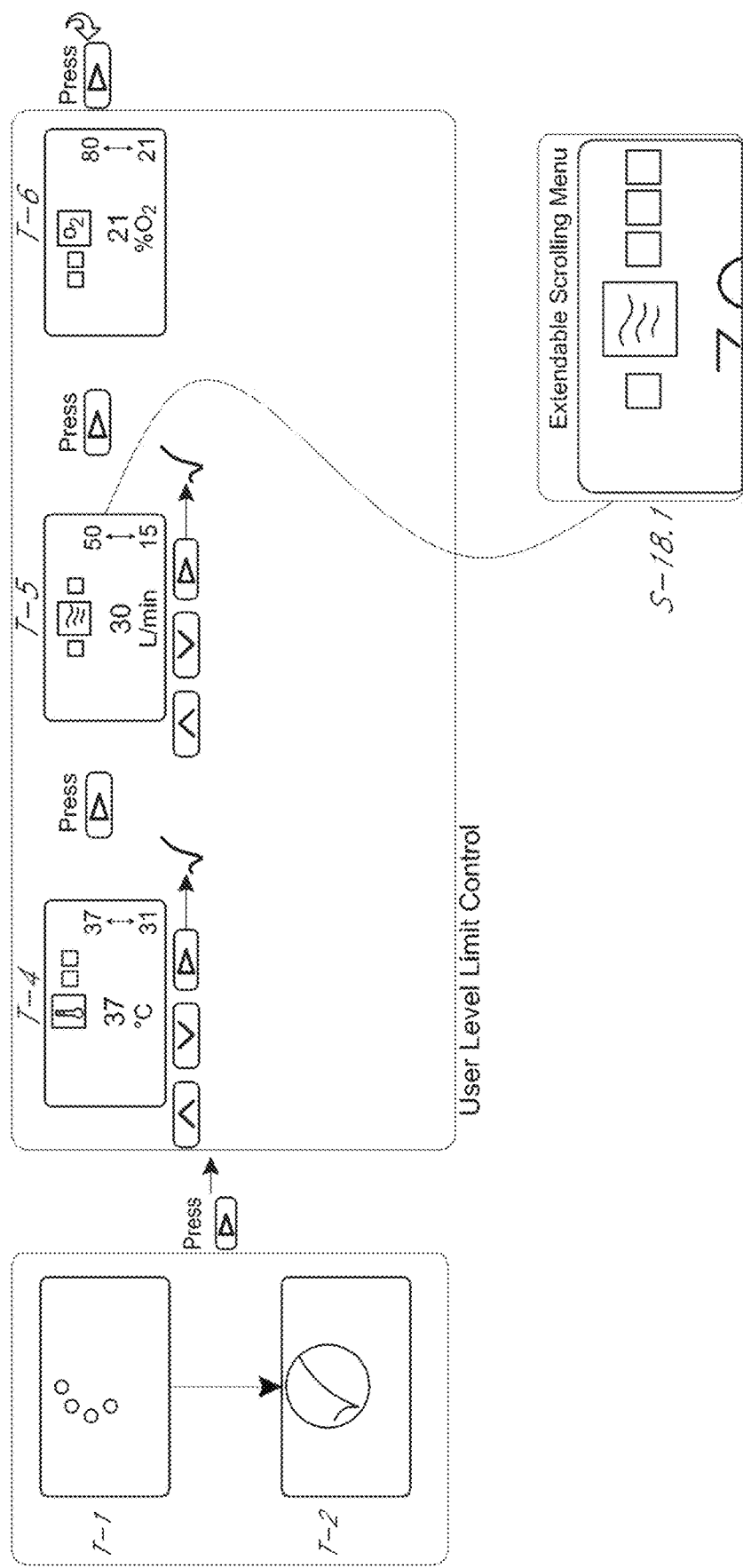
Figure 9C:
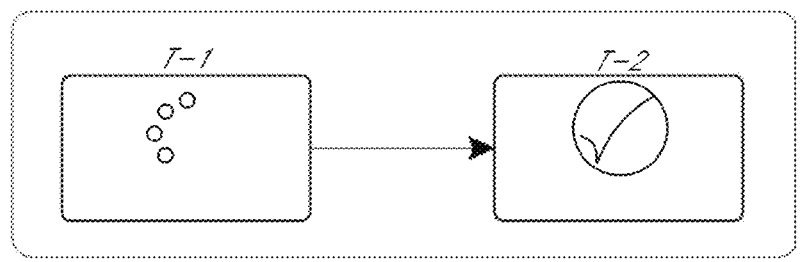
Figure 9C:
Figure 9C:
Figure 9C:
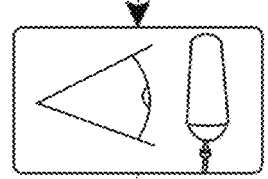
Figure 9C:
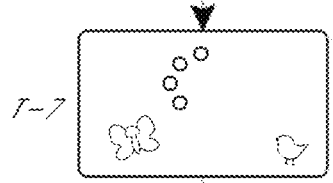
Figure 9C:
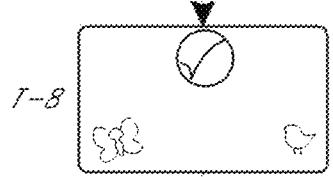
Figure 9C:

As discussed above, the apparatus 22 can be operated in a secondary mode, which can be designed for more intermittent use (e.g., home use). With reference to FIGS. 9A-9C, in the secondary mode, the apparatus 22 operates in many ways similar to the operation of the apparatus 22 in the primary mode. One of the differences, however, relates to the setting of values.

With reference to FIG. 9A, in the illustrated embodiment, the display screen 40 either illustrates the swirling icon (see T-1) discussed above or a checkmark (i.e., tick) (see T-2) also discussed above. As discussed above, current dew point temperature, current flow rate and current oxygen level, for example but without limitation, can be monitored by the apparatus. These values are based upon real time readings. In some embodiments, the readings are made during warm up as well as during use.

In the secondary mode, when the swirling icon (T-1) or the checkmark (T-2) is presented, depressing the mode button 52 will cycle among a plurality of values (T-4, T-5, and T-6), similar to the process depicted in FIG. 6C. The values can be represented by smaller icons or other shapes that, when selected, increase in size and possibly detail. The plurality of smaller icons or other shapes facilitate an expandable scrolling menu that allows a large number of values to be displayed even on a smaller display screen 40, as shown in S-18.1.

While the illustrated configuration depicts a temperature target screen (T-4), a flow rate target screen (T-5) and an oxygen level alarm screen (T-6), any number of additional screens can be presented. In some configurations, a screen can be provided for night-use sub-mode. In the night use sub-mode, non-alarming noises are quieted or cancelled and the brightness of the display screen 40 is adjusted. In some configurations, the apparatus also can display the number of hours, the average hours per day and a value that can be used by a doctor to confirm that accurate numbers are being provided by the user. Moreover, compliance data can be exported using any suitable technique. For example, a serial cable can be plugged into a data port and a USB based modem. Each of these screens can be used to review data or select a value within a preset range. In some embodiments, in the secondary mode, the values are not locked and are easily adjusted without performing an unlocking operation, which can be different from the primary mode as described with reference to FIG. 6C. After a period of inactivity, when adjustments have been made, the apparatus 22 reverts to the swirling icon (see T-1) or the checkmark screen (see T-2).

Comparing FIGS. 6A-6D with FIGS. 9A-9C, another distinction can be shown between the youth sub-mode in the primary mode and the youth sub-mode in the secondary mode. In particular, during warm up (S-22), (T-7) and following warm up (S-23), (T-8), in the primary mode, data is presented regarding various characteristics of operation while, in the secondary mode, the screen does not present the data. This is similar to the screen shown after warm up in the secondary mode (compare S-5 and T-2). While it is possible to present the data in the secondary mode, such data may be less relevant to an intermittent, home-type of user.

Drying Mode in Secondary mode

Following use in the secondary mode, the user presses the power button 42. Upon shut-down, an audible alert is made and the apparatus 22 enters a drying mode. During drying mode, the apparatus 22 turns off power to the heater plate 80, increases the temperature in the conduit 26 by increasing the heat generated by the heater wire 30 and the flow rate is changed to an appropriate value. In some applications, the flow rate is set to about 15 L/min in default mode (e.g., primary mode or secondary mode) or about 10 L/min in the youth sub-modes.

In some configurations, during the drying sub-mode, the apparatus 22, including the conduit 26, is controlled to maintain total enthalpy below a desired enthalpy limit as measured at the patient/user end of the conduit 26. For example, as the chamber cools, the temperature of the conduit 26 can be increased by increasing the heat output of the conduit heater wire 30. In some configurations, the enthalpy limit is less than about 194 kJ/kg dry gas when averaged over 30 seconds. In some configurations, the enthalpy limit is about 194 kJ/Kg dry gas when averaged over 30 seconds.

The drying sub-mode continues for a drying period. At the end of the drying period, the apparatus 22 shuts down.

Fault Conditions

During operation in any of the modes or sub-modes, a number of operating conditions for the apparatus 22 are monitored for fault conditions. Each fault condition that is correctable by a user can be configured to have one or more animations showing the problem and/or how to fix the problem. As described above with respect to replacing the filter (see FIGS. 8A-8D), each animation can comprise a plurality of frames that show slight movement from one frame to the next such that presenting the frames in series provides a visual animation. While certain animations will be discussed below, other animations can be used. Accordingly, the apparatus 22 can be configured to detect fault conditions, select an appropriate animation to display, and detect when the fault condition has been corrected. The selected animation can highlight or indicate the location or components causing the fault condition, illustrate how to correct the fault condition, and provide indicators of success in correcting the fault condition. In some embodiments, the animation only proceeds to a following step when the current step is completed. In some embodiments, the animation is repeated until the fault condition is corrected. In some embodiments, the animation is automatically stopped when the fault condition is corrected. When a fault condition occurs, the apparatus 22 can provide an alarm that can include any combination of audible sounds and visual indicators. The alarm can continue until the fault condition is corrected. For example, the alarm can be configured to automatically cease when the apparatus 22 detects that the problem has been fixed.

In some embodiments, the animations can include a series of images that present "zoomed-in" pictures or animations of the apparatus 22. For example, for selected parts of the animation, the zoomed-in animation can show sections of the apparatus 22 in more detail to illustrate elements that may otherwise be unclear on a display 40 with a relatively low resolution, such as the display 40 that may be included on the apparatus 22. For example, the series of images can include a first subset of images depicting the apparatus 22 with a first level of detail and a second subset of images depicting a second level of detail, the second level of detail being greater than the first level of detail. This second level of detail can be a zoomed-in depiction of the apparatus, and the zoomed-in depiction can be configured to include a region of interest on the apparatus 22 meriting attention.

In some configurations, noises or audible cues can be used in conjunction with the animations. The audible cues can be timed to coincide with the display of actions in the animations. In some embodiments, the audible cues are configured to simulate or approximate a sound that would be produced when the animated action occurs.

In some configurations, flashing lights, colors, glowing effects, and/or other visual cues can be presented in the animations to indicate portions of the address meriting attention (e.g., showing a glowing red effect around a region of interest). These components may be in fault or may be one of the causes of the fault condition that triggered the animation. The visual cues can also be used to indicate the corrected problem, such as how a component should be positioned when it is in the correct location (e.g., showing a glowing green effect around the corrected region of interest). For example, the chamber 70 can be animated to glow red when not properly seated in the apparatus 22, and the animation can illustrate the chamber being correctly positioned and the glowing changing to a green effect.

With reference to FIGS. 8A-8D, if the apparatus 22 detects that a filter replacement is warranted (e.g., if the apparatus 22 detects that it has been in use without a filter replacement for over a minimum number of hours, an example of which is described with reference to U-4 in FIG. 7), the apparatus 22 can display a series of images depicting removal and replacement of a filter. For example, FIGS. 8A-8D depict removal of the filter cover, exposing the filter. Beginning at the bottom of FIG. 8A and into FIG. 8B, the series of images depict the used filter being removed from the apparatus. Beginning at the bottom of FIG. 8B and into FIG. 8C, the series of images depict the new filter being installed into the apparatus. Once the filter is installed, the series of images depict closing the filter cover. The series of images include a zoomed-in depiction of the filter cover being fastened onto the apparatus housing starting in FIG. 8C and into FIG. 8D. The zoomed-in series of images present the filter cover and housing in greater detail to provide more information to the user to enable the user to better close and secure the filter cover in place. In some embodiments, the apparatus 22 can play an audible cue (e.g., a clicking noise or other appropriate sound) to coincide with the depiction of the filter cover being correctly seated or locked-in, as illustrated in the final image in FIG. 8D. The audible cue can be configured to provide the user with an indication of an expected sound to be produced when the animated action is performed correctly.

Figure 10:
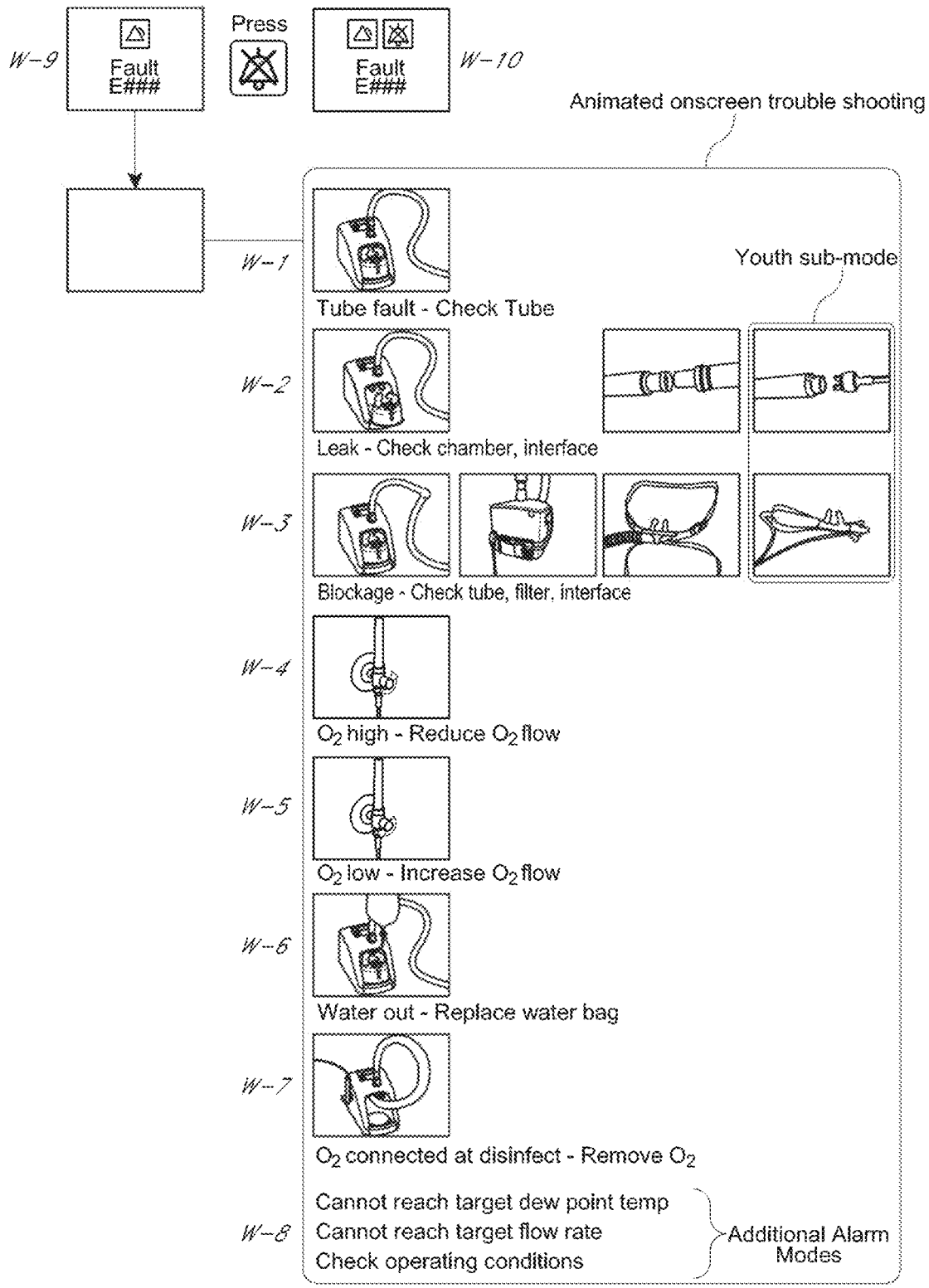
FIG. 10 illustrates a fault condition correction display flow for the apparatus.
Figures 1, 11:
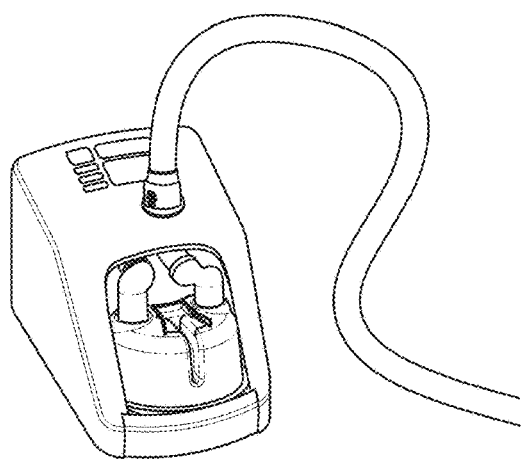
FIG. 11 illustrates a series of images used in an animation showing how to connect a breathing circuit of the apparatus.
Figures 2, 11:
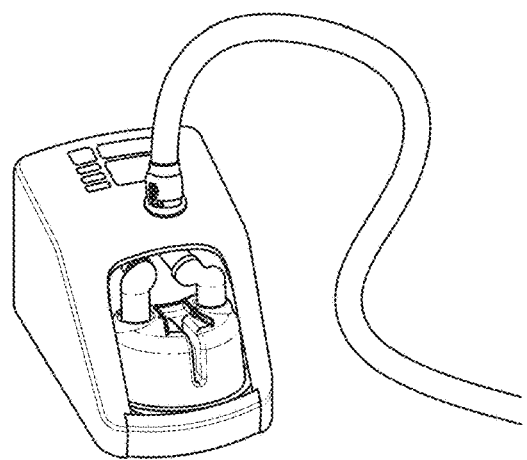
Figures 3, 11:
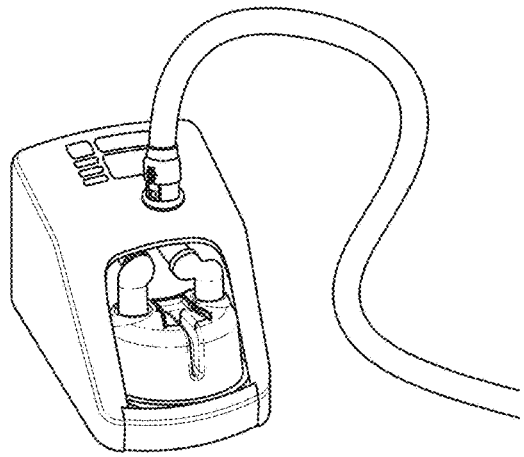
Figures 4, 11:
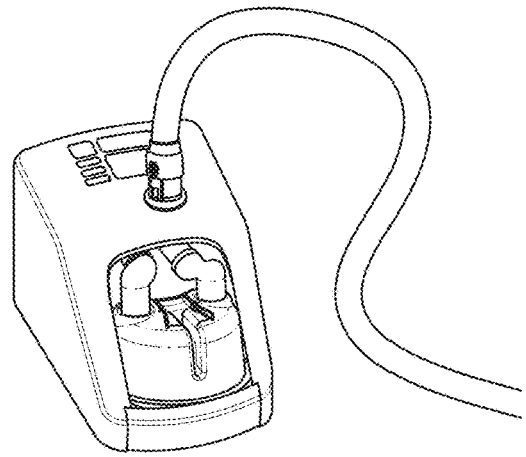
Figures 5, 11:
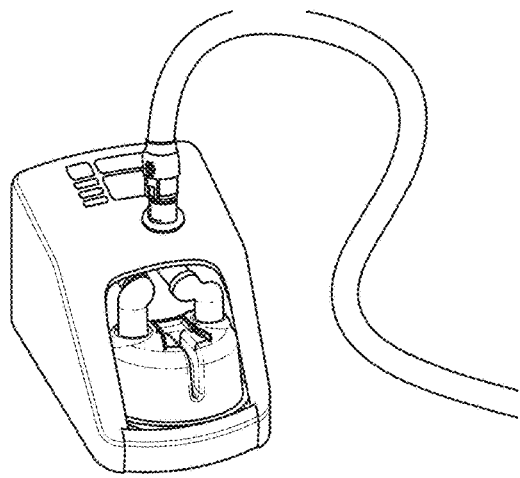
Figures 6, 11:
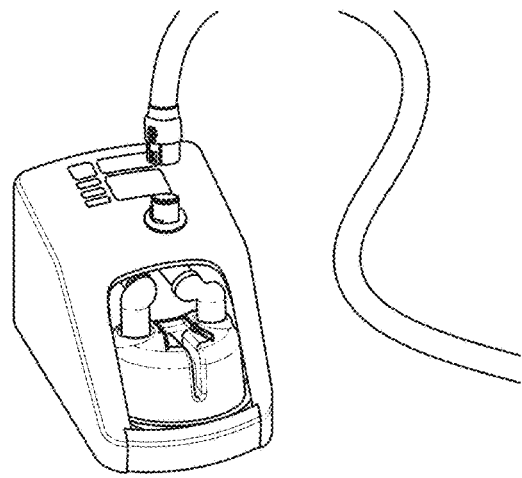

With reference to FIG. 10, if a disconnection from the conduit heater wire is detected, the apparatus indicates a removal of the circuit. See W-1. There can be an audible alarm (e.g., three short monotones, single tone, series of tones, chime, music, etc.) that indicates a disconnection of the circuit. The display can show an animation of the circuit being removed and being reconnected. Some of the images from such an animation are shown in FIG. 11. For example, the series of images in FIG. 11 depict the circuit being removed from the apparatus by disengaging the connector from the outlet end of the elbow and lifting the circuit. In some embodiments, the apparatus 22 can emit an audible cue when the circuit is depicted as being removed from the apparatus. The audible cue can be configured to approximate or simulate a sound that would be produced when disengaging the circuit from the apparatus.

If a loss of resistance to flow is detected (e.g., a system leak, a dislodged interface, a dislodged chamber, etc.), there can be an audible alarm (e.g., three short monotones, single tone, series of tones, chime, music, etc.) that indicates a leak in the system. The display 40 can show an animation or a series of animations. For example but without limitation, the animations can demonstrate reseating the chamber and reseating the interface to the circuit. Similarly, if the apparatus is in the youth sub-mode and an adult cannula is connected, the system indicates a possible leak and issues an audible alarm (e.g., three short monotones, single tone, series of tones, chime, music, etc.). The apparatus 22 also can present an illustration showing the connection of the youth sub-mode cannula (e.g., infant cannula).

If a higher than expected resistance to flow is detected (e.g., a system blockage), there can be an audible alarm (e.g., three short monotones, single tone, series of tones, chime, music, etc.) that indicates a blockage in the system. See W-3. The display 40 can show an animation or a series of animations. For example but without limitation, the animations can demonstrate unkinking a hose, determining if the youth sub-mode interface is installed in the default primary mode or secondary mode, unclogging a nasal cannula, or the like.

If oxygen content is detected above the set level, the system can issue an audible alarm (e.g., three short monotones, single tone, series of tones, chime, music, etc.) and can present an animation illustrating how to decrease the flow of oxygen at the wall connection. See W-4. Similarly, if oxygen content is detected below the set level, the system can issue an audible alarm (e.g., three short monotones, single tone, series of tones, chime, music, etc.) and can present an animation illustrating how to increase the flow of oxygen at the wall connection. See W-5.

If the water level is detected to be low or empty, the system can issue an audible alarm (e.g., three short monotones, single tone, series of tones, chime, music, etc.) and can present an animation illustrating how to remove a depleted water bag and attach a new water bag. See W-6.

If an oxygen supply is detected during operation in the disinfection mode, the apparatus 22 can issue an audible alarm (e.g., three short monotones, single tone, series of tones, chime, music, etc.) and can present an animation illustrating how to remove the oxygen supply. See W-7. In some embodiments, when such a condition is presented, power is not provided to the conduit heater 84 until after the condition has been rectified.

The apparatus 22 might alarm if the apparatus 22 detects a disconnection, depletion or prolonged interruption of the oxygen supply (e.g., if the oxygen level drops below a certain percentage for a preset period of time, if there is a sudden drop or change in the oxygen level or both). In some configurations, the alarm triggering thresholds indicative of oxygen level events can be different in different modes or sub-modes. In some embodiments, when such a condition is presented, the apparatus can issue an audible alarm (e.g., three short monotones, single tone, series of tones, chime, music, etc.) and the display can present an animation illustrating how to check the connection of the oxygen supply.

The apparatus 22 also might alarm if user breathing is no longer detected. In some embodiments, when such a condition is presented, the apparatus can issue an audible alarm (e.g., three short monotones, single tone, series of tones, chime, music, etc.) and the display can present an animation illustrating how to check for a displaced user interface, a disconnected user interface or an adverse clinical event.

The apparatus 22 might alarm if a user breathing rate exceeds a predetermined limit. In some embodiments, when such a condition is presented, the apparatus can issue an audible alarm (e.g., three short tones) and the display can present an animation demonstrating the breathing rate, for example but without limitation.

Any number of other fault conditions also can be detected and other alarms can ensue from such fault conditions. For example, but without limitation, the apparatus 22 might alarm if the target dew point temperature cannot be reached, if the target flow rate cannot be reached, or if there is another operating condition that should be checked and/or corrected. Any or all of these can be indicated with an audible alarm (e.g., three short monotones, single tone, series of tones, chime, music, etc.) and/or an animation or other fault code screen. See W-8. In some embodiments, the audible alarm can be accompanied by animations and the animations and/or the audible alarms can stop automatically when the apparatus 22 detects that the fault conditions has been fixed. Accordingly, the apparatus 22 can be configured to automatically detect the presence and rectification of fault conditions.

The display also can show an international symbol for alarm (e.g., a symbol compliant with IEC 60601-1-8). See W-9. If the mute button is depressed during the alarm, a mute symbol is displayed on the screen and the sound from the alarm can be disabled for a set period of time (e.g., 120 seconds). See W-10. Once any fault condition is resolved, an audible notification can result (e.g., three climbing scale tones) and the system can revert to normal operation.

Thus, in some configurations, the apparatus 22 is configured to prompt users to perform maintenance tasks and troubleshooting through the use of animations or other graphical displays. For example, the apparatus can indicate a desire for a filter replacement as well as coach an individual through changing the filter with a visual representation of the actions to be taken. By way of other examples, the apparatus 22 can indicate how to perform disinfection or how to clean the device.

Moreover, in some configurations, the apparatus 22 can recognize certain fault conditions with the apparatus 20 and coach a person to correct the recognized fault through a video animation of the corrective action or corrective actions desired. For example, where several different causes can underlie a detected loss of resistance to flow, the apparatus 22 can demonstrate several connections and other components to check to restore the anticipated resistance to flow. Where fault codes are primarily used in the apparatus 22 to indicate fault conditions (e.g., E14), it may be problematic for the user 10 to know how to correct the fault based solely upon the fault codes provided by the apparatus 22. Thus, presentation of animations, visual cues, and audible cues can facilitate the rectification of fault conditions.

Figure 12A:
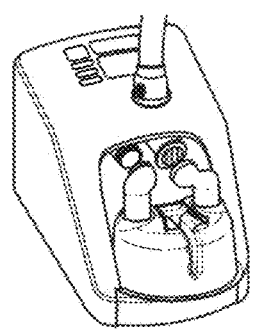
FIGS. 12A-12M illustrate a series of images used in an example animation showing a chamber installation sequence.
Figure 12B:
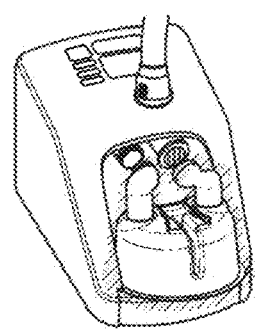
Figure 12C:
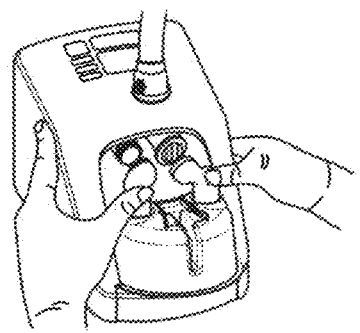
Figure 12D:
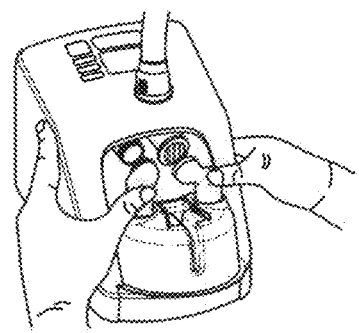
Figure 12E:
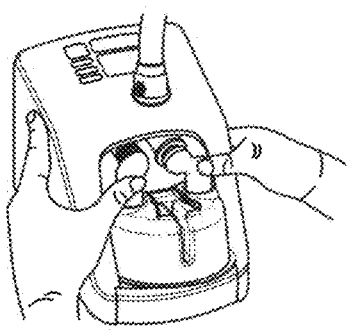
Figure 12F:
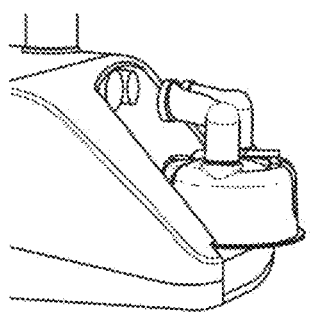
Figure 12G:
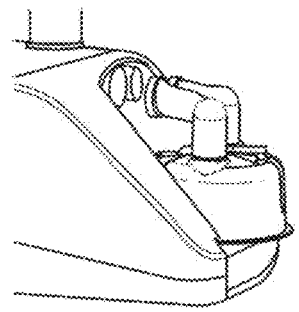
Figure 12H:
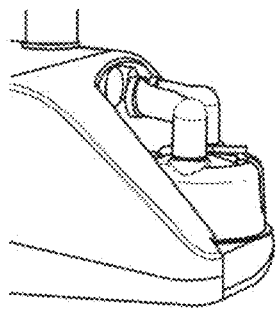
Figure 12I:
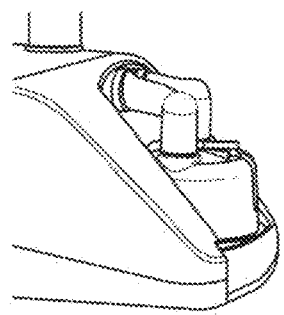
Figure 12J:
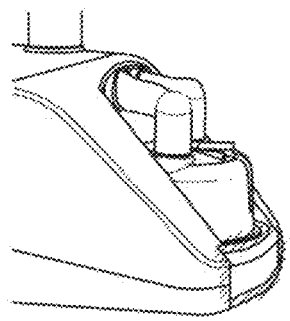
Figure 12K:
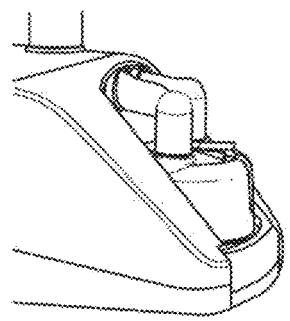
Figure 12L:
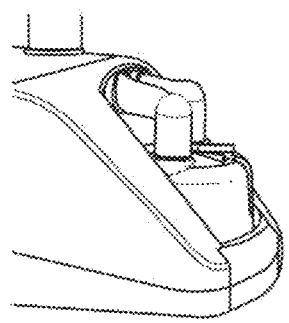
Figure 12M:
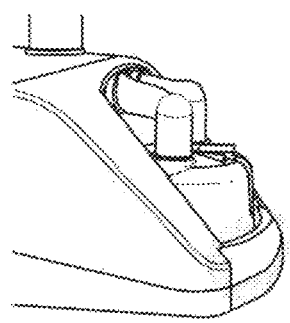

FIGS. 12A-12M illustrates a series of images used in an example animation showing a chamber installation sequence. The animation can be used to indicate a region of interest causing the fault condition. As an example, this is illustrated in FIGS. 12A and 12B which, when alternated, display a flashing glowing region surrounding the chamber. In some embodiments, the flashing glowing region surrounding the chamber is red, but other colors can be used. The animation can continue and display another glowing region indicating an action to be taken by the user. An example of this is shown in FIGS. 12C and 12D which, when alternated, display a flashing glowing region surrounding the user's fingers where force should be applied to the chamber. The flashing glowing region can be colored green to show that this is a correct action, and other colors may be used. The animation can show the result of performing the action indicated in FIGS. 12C-12E, by showing the chamber slide into place in the apparatus (shown in FIGS. 12F-12M). The animation can zoom-in to the apparatus to show greater detail. For example, the animation can zoom-in beginning in FIG. 12F to show the finger guard move into place once the chamber is clear of the guard (as shown in FIG. 12L). Prior to the chamber being clear of the guard, the animation can show the finger guard with a flashing glowing region surrounding it (as shown when FIGS. 12I and 12J are presented in an alternating fashion), and the flashing glowing region can be a first color (e.g., red). When the chamber is correctly positioned, as shown in FIG. 12L, the finger guard can be shown with a differently colored (e.g., green) flashing glowing region (as shown when FIGS. 12L and 12M are presented in an alternating fashion). The animation can be accompanied by an audible cue, such as a clicking sound, when the finger guard moves into position in FIG. 12L. The audible cue can be configured to approximate or simulate the sound of the finger guard clicking into position when the chamber is correctly positioned.

Although the disclosure herein has been presented in terms of some embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice embodiments encompassed by this disclosure. Accordingly, the scope of each of the claimed inventions is intended to be defined only by the claims that follow.

What is claimed is:

1. A breathing assistance apparatus configured to deliver a heated and/or humidified flow of breathing gases to a user via a breathing interface and a conduit, the apparatus comprising:
    a flow generator configured to connect to a humidifier chamber, and
    a display screen adapted to provide visual information to the user,
    wherein the apparatus is configured to operate in at least two modes, one of the modes being a normal mode and another of the modes being a transport mode, the apparatus configured to reduce power usage when operating in the transport mode than in the normal mode,
    wherein, when the apparatus is in the transport mode, the display screen is configured to display a transport mode screen, the transport mode screen comprising an indication of a remaining length of time for which the apparatus will remain in the transport mode, and
    wherein the apparatus is configured to automatically exit the transport mode at the expiration of the remaining length of time.

2. The apparatus of claim 1 wherein the apparatus is configured to reduce the power usage by connecting to a universal power supply ("UPS") when being transported from one location to another, the apparatus not plugged into an electrical wall socket during the transport mode, wherein the UPS is a second power source or a portable power source.

3. The apparatus of claim 1, comprising the humidifier chamber.

4. The apparatus of claim 3, further comprising a heating element configured to heat water in the humidifier chamber, wherein the apparatus is configured to reduce power usage of the heating element when in the transport mode.

5. The apparatus of claim 4, wherein the apparatus is configured to reduce power usage of the heating element when in the transport mode by reducing a temperature setting of the heating element.

6. The apparatus of claim 1, wherein a user temperature set point is reduced from 37 C to 31 C when the apparatus is in the transport mode.

7. The apparatus of claim 1, wherein the flow generator comprises a motor, the apparatus configured to reduce power usage of the motor, when in the transport mode.

8. The apparatus of claim 1, wherein the apparatus is configured to enter the transport mode in response to a manual input from an operator.

9. The apparatus of claim 1, further comprising a mode button, wherein the display screen is configured to display the transport mode screen in response to the mode button being pressed for at least a minimum period of time.

10. The apparatus of claim 1, further comprising up and down buttons, wherein the up and down buttons are configured to be used by an operator to alternate between selecting the normal mode or the transport mode.

11. The apparatus of claim 1, wherein the apparatus is configured to automatically enter the transport mode when connected to a universal power supply (UPS).

12. The apparatus of claim 1, wherein the apparatus is further configured to understand and communicate appropriate handshake protocols with universal power supply (UPS) systems so as to recognize when the apparatus is connected to a UPS rather than an electrical wall socket.

13. The apparatus of claim 12, wherein the apparatus is configured to automatically enter the transport mode upon completing the appropriate handshake protocols with the UPS.

14. The apparatus of claim 1, wherein, when in the transport mode, the apparatus comprises a countdown timer, the display screen configured to display the countdown timer to indicate the remaining length of time for which the apparatus will remain in the transport mode.

15. The apparatus of claim 14, wherein the countdown timer is configured to be reset by the user.

16. The apparatus of claim 1, wherein, after the expiration of the remaining length of time, the apparatus is configure to automatically revert to the normal mode of operation.

17. The apparatus of claim 1, wherein the apparatus is configured to operate in more than two modes and further configured to, after the expiration of the remaining length of time, automatically revert to a mode that the apparatus was in prior to entering the transport mode.

18. The apparatus of claim 1, wherein the display screen is configured to display a temperature setting.

19. The apparatus of claim 1, wherein, when in the transport mode, the display screen is configured to display information or indicators other than the indication of the remaining length of time for which the apparatus will remain in the transport mode, the information or indicators including one or more of a flow rate, an oxygen setting, or a sub mode of the apparatus.

20. The apparatus of claim 1, wherein, prior to the expiration of the remaining length of time, the apparatus is configured to remain in the transport mode until one or both of:

being disconnected from a universal power supply (UPS), or being connected to an electrical wall socket.

21. The apparatus of claim 1, further comprising the conduit, wherein the conduit is configured to connect to the flow generator or the humidifier chamber.

22. The apparatus of claim 21, wherein the conduit comprises a conduit heating element, the apparatus is configured to reduce power usage of the conduit heating element when in the transport mode.

23. The apparatus of claim 21, further comprising the breathing interface, wherein the breathing interface is configured to connect to the conduit.

\* \* \* \* \*